(12) United States Patent
Medina

(10) Patent No.: US 7,880,884 B2
(45) Date of Patent: Feb. 1, 2011

(54) SYSTEM AND METHOD FOR COATING AND SHIELDING ELECTRONIC SENSOR COMPONENTS

(75) Inventor: Casey V. Medina, Lakewood, CO (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 218 days.

(21) Appl. No.: 12/165,133

(22) Filed: Jun. 30, 2008

(65) Prior Publication Data

US 2009/0323067 A1    Dec. 31, 2009

(51) Int. Cl.
*G01N 21/00* (2006.01)
(52) U.S. Cl. .................................... 356/432
(58) Field of Classification Search ............. 356/39, 356/41, 432
See application file for complete search history.

(56) References Cited

U.S. PATENT DOCUMENTS

| | | |
|---|---|---|
| 3,721,813 A | 3/1973 | Condon et al. |
| 4,586,513 A | 5/1986 | Hamaguri |
| 4,603,700 A | 8/1986 | Nichols et al. |
| 4,621,643 A | 11/1986 | New, Jr. et al. |
| 4,653,498 A | 3/1987 | New, Jr. et al. |
| 4,685,464 A | 8/1987 | Goldberger et al. |
| 4,694,833 A | 9/1987 | Hamaguri |
| 4,697,593 A | 10/1987 | Evans et al. |
| 4,700,708 A | 10/1987 | New, Jr. et al. |
| 4,714,080 A | 12/1987 | Edgar, Jr. et al. |
| 4,714,341 A | 12/1987 | Hamaguri et al. |
| 4,726,382 A * | 2/1988 | Boehmer et al. ............ 600/480 |
| 4,759,369 A | 7/1988 | Taylor |
| 4,770,179 A | 9/1988 | New, Jr. et al. |
| 4,773,422 A | 9/1988 | Isaacson et al. |
| 4,776,339 A | 10/1988 | Schreiber |
| 4,781,195 A | 11/1988 | Martin |
| 4,796,636 A | 1/1989 | Branstetter et al. |

(Continued)

FOREIGN PATENT DOCUMENTS

DE    3516338    11/1986

(Continued)

OTHER PUBLICATIONS

Faisst, Karin, et al.; "Intrapartum Reflectance Pulse Oximetry: Effects of Sensor Location and Fixation Duration on Oxygen Saturation Readings," Journal of Clinical Monitoring, vol. 13, pp. 299-302 (1997).

(Continued)

*Primary Examiner*—Roy Punnoose
(74) *Attorney, Agent, or Firm*—Fletcher Yoder

(57) ABSTRACT

Embodiments described herein may include devices and methods of manufacturing sensors for monitoring physiological parameters of a patient. Specifically, embodiments disclose the use of conductive and nonconductive coating materials to increase comfort of sensor and increase accuracy of the parameters measured. The sensor may include a flexible circuit and an optical device with an active face. A generally opaque, nonconductive coating may be disposed over the optical device, except for the active face, which allows for passage of light to the active face. The nonconductive coating may comprise a medical grade silicone of a specified thickness. A second conductive layer may be disposed on a portion of the conductive layer, to provide a Faraday shield for the optical device.

21 Claims, 6 Drawing Sheets

U.S. PATENT DOCUMENTS

| | | | |
|---|---|---|---|
| 4,800,495 A | 1/1989 | Smith | |
| 4,800,885 A | 1/1989 | Johnson | |
| 4,802,486 A | 2/1989 | Goodman et al. | |
| 4,805,623 A | 2/1989 | Jöbsis | |
| 4,807,630 A | 2/1989 | Malinouskas | |
| 4,807,631 A | 2/1989 | Hersh et al. | |
| 4,819,646 A | 4/1989 | Cheung et al. | |
| 4,819,752 A | 4/1989 | Zelin | |
| 4,824,242 A | 4/1989 | Frick et al. | |
| 4,825,872 A * | 5/1989 | Tan et al. | 600/344 |
| 4,825,879 A * | 5/1989 | Tan et al. | 600/344 |
| 4,830,014 A * | 5/1989 | Goodman et al. | 600/310 |
| 4,832,484 A | 5/1989 | Aoyagi et al. | |
| 4,846,183 A | 7/1989 | Martin | |
| 4,848,901 A | 7/1989 | Hood, Jr. | |
| 4,854,699 A | 8/1989 | Edgar, Jr. | |
| 4,859,056 A | 8/1989 | Prosser et al. | |
| 4,859,057 A | 8/1989 | Taylor et al. | |
| 4,863,265 A | 9/1989 | Flower et al. | |
| 4,865,038 A * | 9/1989 | Rich et al. | 600/344 |
| 4,867,557 A | 9/1989 | Takatani et al. | |
| 4,869,253 A | 9/1989 | Craig, Jr. et al. | |
| 4,869,254 A | 9/1989 | Stone et al. | |
| 4,880,304 A | 11/1989 | Jaeb et al. | |
| 4,883,055 A | 11/1989 | Merrick | |
| 4,883,353 A | 11/1989 | Hausman et al. | |
| 4,890,619 A | 1/1990 | Hatschek | |
| 4,892,101 A | 1/1990 | Cheung et al. | |
| 4,901,238 A | 2/1990 | Suzuki et al. | |
| 4,908,762 A | 3/1990 | Suzuki et al. | |
| 4,911,167 A | 3/1990 | Corenman et al. | |
| 4,913,150 A | 4/1990 | Cheung et al. | |
| 4,926,867 A | 5/1990 | Kanda et al. | |
| 4,927,264 A | 5/1990 | Shiga et al. | |
| 4,928,692 A | 5/1990 | Goodman et al. | |
| 4,934,372 A | 6/1990 | Corenman et al. | |
| 4,938,218 A | 7/1990 | Goodman et al. | |
| 4,942,877 A | 7/1990 | Sakai et al. | |
| 4,948,248 A | 8/1990 | Lehman | |
| 4,955,379 A | 9/1990 | Hall | |
| 4,960,126 A | 10/1990 | Conlon et al. | |
| 4,964,408 A * | 10/1990 | Hink et al. | 600/344 |
| 4,971,062 A | 11/1990 | Hasebe et al. | |
| 4,974,591 A | 12/1990 | Awazu et al. | |
| 5,007,423 A | 4/1991 | Branstetter et al. | |
| 5,025,791 A | 6/1991 | Niwa | |
| RE33,643 E | 7/1991 | Isaacson et al. | |
| 5,028,787 A | 7/1991 | Rosenthal et al. | |
| 5,040,039 A | 8/1991 | Hattori et al. | |
| 5,054,488 A | 10/1991 | Muz | |
| 5,055,671 A | 10/1991 | Jones | |
| 5,058,588 A | 10/1991 | Kaestle | |
| 5,065,749 A | 11/1991 | Hasebe et al. | |
| 5,066,859 A | 11/1991 | Karkar et al. | |
| 5,069,213 A | 12/1991 | Polczynksi | |
| 5,078,136 A | 1/1992 | Stone et al. | |
| 5,084,327 A | 1/1992 | Stengel | |
| 5,088,493 A | 2/1992 | Giannini et al. | |
| 5,090,410 A | 2/1992 | Saper et al. | |
| 5,094,239 A | 3/1992 | Jaeb et al. | |
| 5,094,240 A | 3/1992 | Muz | |
| 5,099,841 A | 3/1992 | Heinonen et al. | |
| 5,099,842 A | 3/1992 | Mannheimer et al. | |
| H001039 H | 4/1992 | Tripp et al. | |
| 5,104,623 A | 4/1992 | Miller | |
| 5,109,849 A | 5/1992 | Goodman et al. | |
| 5,111,817 A | 5/1992 | Clark et al. | |
| 5,113,861 A | 5/1992 | Rother | |
| 5,125,403 A | 6/1992 | Culp | |
| 5,127,406 A | 7/1992 | Yamaguchi | |
| 5,131,391 A | 7/1992 | Sakai et al. | |
| 5,140,989 A | 8/1992 | Lewis et al. | |
| 5,152,296 A | 10/1992 | Simons | |
| 5,154,175 A | 10/1992 | Gunther | |
| 5,158,082 A | 10/1992 | Jones | |
| 5,167,230 A | 12/1992 | Chance | |
| 5,170,786 A * | 12/1992 | Thomas et al. | 600/310 |
| 5,188,108 A | 2/1993 | Secker et al. | |
| 5,190,038 A | 3/1993 | Polson et al. | |
| 5,193,542 A | 3/1993 | Missanelli et al. | |
| 5,193,543 A | 3/1993 | Yelderman | |
| 5,203,329 A | 4/1993 | Takatani et al. | |
| 5,209,230 A | 5/1993 | Swedlow et al. | |
| 5,213,099 A | 5/1993 | Tripp et al. | |
| 5,216,598 A | 6/1993 | Branstetter et al. | |
| 5,217,012 A * | 6/1993 | Young et al. | 600/310 |
| 5,217,013 A * | 6/1993 | Lewis et al. | 600/342 |
| 5,218,962 A | 6/1993 | Mannheimer et al. | |
| 5,224,478 A | 7/1993 | Sakai et al. | |
| 5,226,417 A | 7/1993 | Swedlow et al. | |
| 5,228,440 A | 7/1993 | Chung et al. | |
| 5,237,994 A * | 8/1993 | Goldberger | 600/323 |
| 5,239,185 A | 8/1993 | Ito et al. | |
| 5,246,002 A | 9/1993 | Prosser | |
| 5,246,003 A | 9/1993 | DeLonzor | |
| 5,247,931 A | 9/1993 | Norwood | |
| 5,247,932 A | 9/1993 | Chung et al. | |
| 5,249,576 A | 10/1993 | Goldberger et al. | |
| 5,253,645 A | 10/1993 | Freidman et al. | |
| 5,253,646 A | 10/1993 | Delpy et al. | |
| 5,259,381 A | 11/1993 | Cheung et al. | |
| 5,259,761 A | 11/1993 | Schnettler et al. | |
| 5,263,244 A | 11/1993 | Centa et al. | |
| 5,267,562 A | 12/1993 | Ukawa et al. | |
| 5,267,563 A | 12/1993 | Swedlow et al. | |
| 5,273,036 A | 12/1993 | Kronberg et al. | |
| 5,275,159 A | 1/1994 | Griebel | |
| 5,279,295 A | 1/1994 | Martens et al. | |
| 5,285,783 A | 2/1994 | Secker | |
| 5,285,784 A | 2/1994 | Seeker | |
| 5,287,853 A | 2/1994 | Vester et al. | |
| 5,291,884 A | 3/1994 | Heinemann et al. | |
| 5,297,548 A | 3/1994 | Pologe | |
| 5,299,120 A | 3/1994 | Kaestle | |
| 5,299,570 A | 4/1994 | Hatschek | |
| 5,309,908 A | 5/1994 | Freidman et al. | |
| 5,311,865 A | 5/1994 | Mayeux | |
| 5,313,940 A | 5/1994 | Fuse et al. | |
| 5,323,776 A | 6/1994 | Blakely et al. | |
| 5,329,922 A | 7/1994 | Atlee, III | |
| 5,337,744 A | 8/1994 | Branigan | |
| 5,339,810 A | 8/1994 | Ivers et al. | |
| 5,343,818 A | 9/1994 | McCarthy et al. | |
| 5,343,869 A | 9/1994 | Pross et al. | |
| 5,348,003 A | 9/1994 | Caro | |
| 5,348,004 A | 9/1994 | Hollub et al. | |
| 5,349,519 A | 9/1994 | Kaestle | |
| 5,349,952 A | 9/1994 | McCarthy et al. | |
| 5,349,953 A | 9/1994 | McCarthy et al. | |
| 5,351,685 A | 10/1994 | Potratz | |
| 5,353,799 A | 10/1994 | Chance | |
| 5,355,880 A | 10/1994 | Thomas et al. | |
| 5,355,882 A | 10/1994 | Ukawa et al. | |
| 5,358,519 A * | 10/1994 | Grandjean | 623/3.12 |
| 5,361,758 A | 11/1994 | Hall et al. | |
| 5,365,066 A | 11/1994 | Krueger, Jr. et al. | |
| 5,368,025 A * | 11/1994 | Young et al. | 600/310 |
| 5,368,026 A | 11/1994 | Swedlow et al. | |
| 5,368,224 A | 11/1994 | Richardson et al. | |
| 5,372,136 A | 12/1994 | Steuer et al. | |
| 5,377,675 A | 1/1995 | Ruskewicz et al. | |
| 5,385,143 A | 1/1995 | Aoyagi | |
| 5,387,122 A | 2/1995 | Goldberger et al. | |
| 5,390,670 A * | 2/1995 | Centa et al. | 600/310 |

| | | | | | | |
|---|---|---|---|---|---|---|
| 5,392,777 | A | 2/1995 | Swedlow et al. | 5,645,060 | A | 7/1997 | Yorkey et al. |
| 5,398,680 | A | 3/1995 | Polson et al. | 5,645,440 | A | 7/1997 | Tobler et al. |
| 5,402,777 | A | 4/1995 | Warring et al. | 5,660,567 | A | 8/1997 | Nierlich et al. |
| 5,411,023 | A | 5/1995 | Morris, Sr. et al. | 5,662,105 | A | 9/1997 | Tien |
| 5,411,024 | A | 5/1995 | Thomas et al. | 5,662,106 | A | 9/1997 | Swedlow et al. |
| 5,413,099 | A | 5/1995 | Schmidt et al. | 5,666,952 | A | 9/1997 | Fuse et al. |
| 5,413,100 | A | 5/1995 | Barthelemy et al. | 5,671,529 | A | 9/1997 | Nelson |
| 5,413,101 | A | 5/1995 | Sugiura | 5,673,692 | A | 10/1997 | Schulze et al. |
| 5,413,102 | A | 5/1995 | Schmidt et al. | 5,673,693 | A | 10/1997 | Solenberger |
| 5,417,207 | A | 5/1995 | Young et al. | 5,676,139 | A | 10/1997 | Goldberger et al. |
| 5,421,329 | A | 6/1995 | Casciani et al. | 5,676,141 | A | 10/1997 | Hollub |
| 5,425,360 | A | 6/1995 | Nelson | 5,678,544 | A | 10/1997 | DeLonzor et al. |
| 5,425,362 | A | 6/1995 | Siker et al. | 5,680,857 | A | 10/1997 | Pelikan et al. |
| 5,427,093 | A | 6/1995 | Ogawa et al. | 5,685,299 | A | 11/1997 | Diab et al. |
| 5,429,128 | A | 7/1995 | Cadell et al. | 5,685,301 | A | 11/1997 | Klomhaus |
| 5,429,129 | A * | 7/1995 | Lovejoy et al. ............. 600/310 | 5,687,719 | A | 11/1997 | Sato et al. |
| 5,431,159 | A | 7/1995 | Baker et al. | 5,687,722 | A | 11/1997 | Tien et al. |
| 5,431,170 | A | 7/1995 | Mathews | 5,692,503 | A | 12/1997 | Kuenstner |
| 5,437,275 | A | 8/1995 | Amundsen et al. | 5,692,505 | A | 12/1997 | Fouts |
| 5,438,986 | A | 8/1995 | Disch et al. | 5,709,205 | A | 1/1998 | Bukta |
| 5,448,991 | A | 9/1995 | Polson et al. | 5,713,355 | A | 2/1998 | Richardson et al. |
| 5,452,717 | A | 9/1995 | Branigan et al. | 5,724,967 | A | 3/1998 | Venkatachalam |
| 5,465,714 | A | 11/1995 | Scheuing | 5,727,547 | A | 3/1998 | Levinson et al. |
| 5,469,845 | A * | 11/1995 | DeLonzor et al. ........... 600/372 | 5,731,582 | A | 3/1998 | West |
| RE35,122 | E | 12/1995 | Corenman et al. | D393,830 | S | 4/1998 | Tobler et al. |
| 5,482,034 | A * | 1/1996 | Lewis et al. ................. 600/323 | 5,743,260 | A | 4/1998 | Chung et al. |
| 5,482,036 | A | 1/1996 | Diab et al. | 5,743,263 | A | 4/1998 | Baker, Jr. |
| 5,483,646 | A | 1/1996 | Uchikoga | 5,746,206 | A | 5/1998 | Mannheimer |
| 5,485,847 | A | 1/1996 | Baker, Jr. | 5,746,697 | A | 5/1998 | Swedlow et al. |
| 5,490,505 | A | 2/1996 | Diab et al. | 5,752,914 | A | 5/1998 | Delonzor et al. |
| 5,490,523 | A | 2/1996 | Isaacson et al. | 5,755,226 | A | 5/1998 | Carim et al. |
| 5,491,299 | A | 2/1996 | Naylor et al. | 5,758,644 | A | 6/1998 | Diab et al. |
| 5,494,032 | A | 2/1996 | Robinson et al. | 5,760,910 | A | 6/1998 | Lepper, Jr. et al. |
| 5,497,771 | A | 3/1996 | Rosenheimer | 5,766,125 | A | 6/1998 | Aoyagi et al. |
| 5,499,627 | A * | 3/1996 | Steuer et al. ................. 600/322 | 5,766,127 | A | 6/1998 | Pologe et al. |
| 5,503,148 | A | 4/1996 | Pologe et al. | 5,769,785 | A | 6/1998 | Diab et al. |
| 5,505,199 | A | 4/1996 | Kim | 5,772,587 | A | 6/1998 | Gratton et al. |
| 5,507,286 | A | 4/1996 | Solenberger | 5,774,213 | A | 6/1998 | Trebino et al. |
| 5,517,988 | A | 5/1996 | Gerhard | 5,776,058 | A | 7/1998 | Levinson et al. |
| 5,520,177 | A | 5/1996 | Ogawa et al. | 5,776,059 | A | 7/1998 | Kaestle |
| 5,521,851 | A | 5/1996 | Wei et al. | 5,779,630 | A | 7/1998 | Fein et al. |
| 5,522,388 | A | 6/1996 | Ishikawa et al. | 5,779,631 | A | 7/1998 | Chance |
| 5,524,617 | A | 6/1996 | Mannheimer | 5,782,237 | A | 7/1998 | Casciani et al. |
| 5,529,064 | A | 6/1996 | Rall et al. | 5,782,756 | A | 7/1998 | Mannheimer |
| 5,533,507 | A | 7/1996 | Potratz et al. | 5,782,757 | A | 7/1998 | Diab et al. |
| 5,551,423 | A | 9/1996 | Sugiura | 5,782,758 | A | 7/1998 | Ausec et al. |
| 5,551,424 | A | 9/1996 | Morrison et al. | 5,786,592 | A | 7/1998 | Hök |
| 5,553,614 | A | 9/1996 | Chance | 5,790,729 | A | 8/1998 | Pologe et al. |
| 5,553,615 | A | 9/1996 | Carim et al. | 5,792,052 | A | 8/1998 | Isaacson et al. |
| 5,555,882 | A | 9/1996 | Richardson et al. | 5,795,292 | A | 8/1998 | Lewis et al. |
| 5,558,096 | A | 9/1996 | Palatnik | 5,797,841 | A | 8/1998 | DeLonzor et al. |
| 5,560,355 | A | 10/1996 | Merchant et al. | 5,800,348 | A | 9/1998 | Kaestle |
| 5,564,417 | A | 10/1996 | Chance | 5,800,349 | A | 9/1998 | Isaacson et al. |
| 5,575,284 | A | 11/1996 | Athan et al. | 5,803,910 | A | 9/1998 | Potratz |
| 5,575,285 | A | 11/1996 | Takanashi et al. | 5,807,246 | A | 9/1998 | Sakaguchi et al. |
| 5,577,500 | A | 11/1996 | Potratz | 5,807,247 | A | 9/1998 | Merchant et al. |
| 5,582,169 | A | 12/1996 | Oda et al. | 5,807,248 | A | 9/1998 | Mills |
| 5,584,296 | A * | 12/1996 | Cui et al. ..................... 600/479 | 5,810,723 | A | 9/1998 | Aldrich |
| 5,588,425 | A | 12/1996 | Sackner et al. | 5,810,724 | A | 9/1998 | Gronvall |
| 5,588,427 | A | 12/1996 | Tien | 5,813,980 | A | 9/1998 | Levinson et al. |
| 5,590,652 | A | 1/1997 | Inai | 5,817,008 | A * | 10/1998 | Rafert et al. ................. 600/323 |
| 5,595,176 | A | 1/1997 | Yamaura | 5,817,009 | A | 10/1998 | Rosenheimer et al. |
| 5,596,986 | A | 1/1997 | Goldfarb | 5,817,010 | A | 10/1998 | Hibl |
| 5,611,337 | A | 3/1997 | Bukta | 5,818,985 | A | 10/1998 | Merchant et al. |
| 5,617,852 | A | 4/1997 | MacGregor | 5,820,550 | A | 10/1998 | Polson et al. |
| 5,619,992 | A | 4/1997 | Guthrie et al. | 5,823,950 | A | 10/1998 | Diab et al. |
| 5,626,140 | A | 5/1997 | Feldman et al. | 5,823,952 | A | 10/1998 | Levinson et al. |
| 5,630,413 | A | 5/1997 | Thomas et al. | 5,827,182 | A | 10/1998 | Raley et al. |
| 5,632,272 | A | 5/1997 | Diab et al. | 5,830,135 | A | 11/1998 | Bosque et al. |
| 5,632,273 | A | 5/1997 | Suzuki | 5,830,136 | A | 11/1998 | DeLonzor et al. |
| 5,634,459 | A | 6/1997 | Gardosi | 5,830,137 | A | 11/1998 | Scharf |
| 5,638,593 | A | 6/1997 | Gerhardt et al. | 5,839,439 | A | 11/1998 | Nierlich et al. |
| 5,638,818 | A | 6/1997 | Diab et al. | RE36,000 | E * | 12/1998 | Swedlow et al. ............. 600/454 |

| | | | | | |
|---|---|---|---|---|---|
| 5,842,979 A | 12/1998 | Jarman et al. | 6,064,898 A | 5/2000 | Aldrich |
| 5,842,981 A | 12/1998 | Larsen et al. | 6,064,899 A | 5/2000 | Fein et al. |
| 5,842,982 A | 12/1998 | Mannheimer | 6,067,462 A | 5/2000 | Diab et al. |
| 5,846,190 A | 12/1998 | Woehrle | 6,073,038 A | 6/2000 | Wang et al. |
| 5,851,178 A | 12/1998 | Aronow | 6,078,833 A | 6/2000 | Hueber |
| 5,851,179 A | 12/1998 | Ritson et al. | 6,081,735 A | 6/2000 | Diab et al. |
| 5,853,364 A | 12/1998 | Baker, Jr. et al. | 6,081,742 A | 6/2000 | Amano et al. |
| 5,860,919 A | 1/1999 | Kiani-Azarbayjany et al. | 6,083,157 A | 7/2000 | Noller |
| 5,865,736 A | 2/1999 | Baker, Jr. et al. | 6,083,172 A | 7/2000 | Baker, Jr. et al. |
| 5,871,442 A | 2/1999 | Madarasz et al. | 6,088,607 A | 7/2000 | Diab et al. |
| 5,879,294 A | 3/1999 | Anderson et al. | 6,094,592 A | 7/2000 | Yorkey et al. |
| 5,885,213 A | 3/1999 | Richardson et al. | 6,095,974 A | 8/2000 | Shemwell et al. |
| 5,890,929 A | 4/1999 | Mills et al. | 6,104,938 A | 8/2000 | Huiku et al. |
| 5,891,021 A | 4/1999 | Dillon et al. | 6,112,107 A | 8/2000 | Hannula |
| 5,891,022 A | 4/1999 | Pologe | 6,113,541 A | 9/2000 | Dias et al. |
| 5,891,024 A | 4/1999 | Jarman et al. | 6,115,621 A | 9/2000 | Chin |
| 5,891,025 A | 4/1999 | Buschmann et al. | 6,122,535 A | 9/2000 | Kaestle et al. |
| 5,891,026 A | 4/1999 | Wang et al. | 6,133,994 A | 10/2000 | Mathews et al. |
| 5,902,235 A | 5/1999 | Lewis et al. | 6,135,952 A | 10/2000 | Coetzee |
| 5,910,108 A | 6/1999 | Solenberger | 6,144,444 A | 11/2000 | Haworth et al. |
| 5,911,690 A | 6/1999 | Rall | 6,144,867 A | 11/2000 | Walker et al. |
| 5,912,656 A | 6/1999 | Tham et al. | 6,144,868 A | 11/2000 | Parker |
| 5,913,819 A | 6/1999 | Taylor et al. | 6,149,481 A | 11/2000 | Wang et al. |
| 5,916,154 A | 6/1999 | Hobbs et al. | 6,150,951 A | 11/2000 | Olejniczak |
| 5,916,155 A | 6/1999 | Levinson et al. | 6,151,107 A | 11/2000 | Schöllerman et al. |
| 5,919,133 A | 7/1999 | Taylor et al. | 6,151,518 A | 11/2000 | Hayashi |
| 5,919,134 A | 7/1999 | Diab | 6,152,754 A | 11/2000 | Gerhardt et al. |
| 5,920,263 A | 7/1999 | Huttenhoff et al. | 6,154,667 A | 11/2000 | Miura et al. |
| 5,921,921 A | 7/1999 | Potratz et al. | 6,157,850 A | 12/2000 | Diab et al. |
| 5,922,607 A | 7/1999 | Bernreuter | 6,163,175 A | 12/2000 | Sharpe-Geisler |
| 5,924,979 A | 7/1999 | Swedlow et al. | 6,163,715 A | 12/2000 | Sharpe-Geisler |
| 5,924,980 A | 7/1999 | Coetzee | 6,165,005 A | 12/2000 | Mills et al. |
| 5,924,982 A | 7/1999 | Chin | 6,173,196 B1 | 1/2001 | Delonzor et al. |
| 5,924,985 A | 7/1999 | Jones | 6,178,343 B1 | 1/2001 | Bindszus et al. |
| 5,934,277 A | 8/1999 | Mortz | 6,181,958 B1 | 1/2001 | Steuer et al. |
| 5,934,925 A | 8/1999 | Tobler et al. | 6,181,959 B1 | 1/2001 | Schöllerman et al. |
| 5,940,182 A | 8/1999 | Lepper, Jr. et al. | 6,184,521 B1 | 2/2001 | Coffin, IV et al. |
| 5,954,644 A | 9/1999 | Dettling et al. | 6,188,470 B1 | 2/2001 | Grace |
| 5,960,610 A | 10/1999 | Levinson et al. | 6,192,260 B1 | 2/2001 | Chance |
| 5,961,450 A | 10/1999 | Merchant et al. | 6,195,575 B1 | 2/2001 | Levinson |
| 5,961,452 A | 10/1999 | Chung et al. | 6,198,951 B1 | 3/2001 | Kosuda et al. |
| 5,964,701 A | 10/1999 | Asada et al. | 6,206,830 B1 | 3/2001 | Diab et al. |
| 5,971,930 A | 10/1999 | Elghazzawi | 6,213,952 B1 | 4/2001 | Finarov et al. |
| 5,978,691 A | 11/1999 | Mills | 6,217,523 B1 | 4/2001 | Amano et al. |
| 5,978,693 A | 11/1999 | Hamilton et al. | 6,222,189 B1 | 4/2001 | Misner et al. |
| 5,983,122 A | 11/1999 | Jarman et al. | 6,226,539 B1 | 5/2001 | Potratz |
| 5,987,343 A | 11/1999 | Kinast | 6,226,540 B1 | 5/2001 | Bernreuter et al. |
| 5,991,648 A | 11/1999 | Levin | 6,229,856 B1 | 5/2001 | Diab et al. |
| 5,995,855 A | 11/1999 | Kiani et al. | 6,230,035 B1 | 5/2001 | Aoyagi et al. |
| 5,995,856 A | 11/1999 | Mannheimer et al. | 6,233,470 B1 | 5/2001 | Tsuchiya |
| 5,995,858 A | 11/1999 | Kinast | 6,236,871 B1 | 5/2001 | Tsuchiya |
| 5,995,859 A | 11/1999 | Takahashi | 6,236,872 B1 | 5/2001 | Diab et al. |
| 5,997,343 A | 12/1999 | Mills et al. | 6,240,305 B1 | 5/2001 | Tsuchiya |
| 5,999,834 A | 12/1999 | Wang et al. | 6,253,097 B1 | 6/2001 | Aronow et al. |
| 6,002,952 A | 12/1999 | Diab et al. | 6,253,098 B1 | 6/2001 | Walker et al. |
| 6,005,658 A | 12/1999 | Kaluza et al. | 6,256,523 B1 | 7/2001 | Diab et al. |
| 6,006,120 A | 12/1999 | Levin | 6,256,524 B1 | 7/2001 | Walker et al. |
| 6,011,985 A | 1/2000 | Athan et al. | 6,261,236 B1 | 7/2001 | Grimblatov |
| 6,011,986 A | 1/2000 | Diab et al. | 6,263,221 B1 | 7/2001 | Chance et al. |
| 6,014,576 A | 1/2000 | Raley et al. | 6,263,222 B1 | 7/2001 | Diab et al. |
| 6,018,673 A * | 1/2000 | Chin et al. ................. 600/322 | 6,263,223 B1 | 7/2001 | Sheperd et al. |
| 6,018,674 A | 1/2000 | Aronow | 6,266,546 B1 | 7/2001 | Steuer et al. |
| 6,022,321 A | 2/2000 | Amano et al. | 6,266,547 B1 | 7/2001 | Walker et al. |
| 6,023,541 A | 2/2000 | Merchant et al. | 6,272,363 B1 | 8/2001 | Casciani et al. |
| 6,026,312 A | 2/2000 | Shemwell et al. | 6,278,522 B1 | 8/2001 | Lepper, Jr. et al. |
| 6,026,314 A | 2/2000 | Amerov et al. | 6,280,213 B1 | 8/2001 | Tobler et al. |
| 6,031,603 A | 2/2000 | Fine et al. | 6,280,381 B1 | 8/2001 | Malin et al. |
| 6,035,223 A | 3/2000 | Baker, Jr. | 6,285,894 B1 | 9/2001 | Oppelt et al. |
| 6,036,642 A | 3/2000 | Diab et al. | 6,285,895 B1 | 9/2001 | Ristolainen et al. |
| 6,041,247 A | 3/2000 | Weckstrom et al. | 6,285,896 B1 | 9/2001 | Tobler et al. |
| 6,044,283 A | 3/2000 | Fein et al. | 6,298,252 B1 | 10/2001 | Kovach et al. |
| 6,047,201 A | 4/2000 | Jackson, III | 6,308,089 B1 | 10/2001 | Von der Ruhr et al. |
| 6,061,584 A | 5/2000 | Lovejoy et al. | 6,321,100 B1 | 11/2001 | Parker |

| Patent | Date | Inventor |
|---|---|---|
| 6,330,468 B1 | 12/2001 | Scharf |
| 6,334,065 B1 | 12/2001 | Al-Ali et al. |
| 6,339,715 B1 | 1/2002 | Bahr et al. |
| 6,343,223 B1 | 1/2002 | Chin et al. |
| 6,343,224 B1 | 1/2002 | Parker |
| 6,349,228 B1 | 2/2002 | Kiani et al. |
| 6,351,658 B1 | 2/2002 | Middleman et al. |
| 6,353,750 B1 | 3/2002 | Kimura et al. |
| 6,356,774 B1 | 3/2002 | Bernstein et al. |
| 6,360,113 B1 | 3/2002 | Dettling |
| 6,360,114 B1 | 3/2002 | Diab et al. |
| 6,361,501 B1 | 3/2002 | Amano et al. |
| 6,363,269 B1 | 3/2002 | Hanna et al. |
| 6,370,408 B1 | 4/2002 | Merchant et al. |
| 6,370,409 B1 | 4/2002 | Chung et al. |
| 6,374,129 B1 | 4/2002 | Chin et al. |
| 6,377,829 B1 | 4/2002 | Al-Ali et al. |
| 6,381,479 B1 | 4/2002 | Norris |
| 6,381,480 B1 | 4/2002 | Stoddar et al. |
| 6,385,471 B1 | 5/2002 | Mortz |
| 6,385,821 B1 | 5/2002 | Modgil et al. |
| 6,388,240 B2 | 5/2002 | Schulz et al. |
| 6,393,310 B1 | 5/2002 | Kuenster |
| 6,397,091 B2 | 5/2002 | Diab et al. |
| 6,397,092 B1 | 5/2002 | Norris et al. |
| 6,397,093 B1 | 5/2002 | Aldrich |
| 6,400,971 B1 | 6/2002 | Finarov et al. |
| 6,400,972 B1 | 6/2002 | Fine |
| 6,402,690 B1 | 6/2002 | Rhee et al. |
| 6,408,198 B1 | 6/2002 | Hanna et al. |
| 6,411,832 B1 | 6/2002 | Guthermann |
| 6,411,833 B1 | 6/2002 | Baker, Jr. et al. |
| 6,419,671 B1 | 7/2002 | Lemberg |
| 6,421,549 B1 | 7/2002 | Jacques |
| 6,430,423 B2 | 8/2002 | DeLonzor et al. |
| 6,430,513 B1 | 8/2002 | Wang et al. |
| 6,430,525 B1 | 8/2002 | Weber et al. |
| 6,434,408 B1 | 8/2002 | Heckel et al. |
| 6,438,399 B1 | 8/2002 | Kurth |
| 6,449,501 B1 | 9/2002 | Reuss |
| 6,453,183 B1 | 9/2002 | Walker |
| 6,453,184 B1 | 9/2002 | Hyogo et al. |
| 6,456,862 B2 | 9/2002 | Benni |
| 6,461,305 B1 | 10/2002 | Schnall |
| 6,463,310 B1 | 10/2002 | Swedlow et al. |
| 6,463,311 B1 | 10/2002 | Diab |
| 6,466,808 B1 | 10/2002 | Chin et al. |
| 6,466,809 B1 | 10/2002 | Riley |
| 6,470,199 B1 | 10/2002 | Kopotic et al. |
| 6,470,200 B2 | 10/2002 | Walker et al. |
| 6,480,729 B2 | 11/2002 | Stone |
| 6,490,466 B1 | 12/2002 | Fein et al. |
| 6,496,711 B1 | 12/2002 | Athan et al. |
| 6,498,942 B1 | 12/2002 | Esenaliev et al. |
| 6,501,974 B2 | 12/2002 | Huiku |
| 6,501,975 B2 | 12/2002 | Diab et al. |
| 6,505,060 B1 | 1/2003 | Norris |
| 6,505,061 B1 | 1/2003 | Larson |
| 6,505,133 B1 | 1/2003 | Hanna et al. |
| 6,510,329 B2 | 1/2003 | Heckel |
| 6,510,331 B1 | 1/2003 | Williams et al. |
| 6,512,937 B2 | 1/2003 | Blank et al. |
| 6,515,273 B2 | 2/2003 | Al-Ali |
| 6,519,484 B1 | 2/2003 | Lovejoy et al. |
| 6,519,486 B1 | 2/2003 | Edgar, Jr. et al. |
| 6,519,487 B1 | 2/2003 | Parker |
| 6,525,386 B1 | 2/2003 | Mills et al. |
| 6,526,300 B1 | 2/2003 | Kiani et al. |
| 6,526,301 B2 | 2/2003 | Larsen et al. |
| 6,541,756 B2 | 4/2003 | Schulz et al. |
| 6,542,764 B1 | 4/2003 | Al-Ali et al. |
| 6,546,267 B1 | 4/2003 | Sugiura et al. |
| 6,553,241 B2 | 4/2003 | Mannheimer et al. |
| 6,553,242 B1 | 4/2003 | Sarussi |
| 6,553,243 B2 | 4/2003 | Gurley |
| 6,556,852 B1 | 4/2003 | Schulze et al. |
| 6,560,470 B1 | 5/2003 | Pologe |
| 6,564,077 B2 | 5/2003 | Mortara |
| 6,564,088 B1 | 5/2003 | Soller et al. |
| 6,571,113 B1 | 5/2003 | Fein et al. |
| 6,571,114 B1 | 5/2003 | Koike et al. |
| 6,574,491 B2 | 6/2003 | Elghazzawi |
| 6,580,086 B1 | 6/2003 | Schulz et al. |
| 6,584,336 B1 | 6/2003 | Ali et al. |
| 6,587,703 B2 | 7/2003 | Cheng et al. |
| 6,587,704 B1 | 7/2003 | Fine et al. |
| 6,589,172 B2 | 7/2003 | Williams et al. |
| 6,591,122 B2 | 7/2003 | Schmitt |
| 6,591,123 B2 | 7/2003 | Fein et al. |
| 6,594,511 B2 | 7/2003 | Stone et al. |
| 6,594,512 B2 | 7/2003 | Huang |
| 6,594,513 B1 | 7/2003 | Jobsis et al. |
| 6,596,016 B1 | 7/2003 | Vreman et al. |
| 6,597,931 B1 | 7/2003 | Cheng et al. |
| 6,597,933 B2 | 7/2003 | Kiani et al. |
| 6,600,940 B1 | 7/2003 | Fein et al. |
| 6,606,510 B2 | 8/2003 | Swedlow et al. |
| 6,606,511 B1 | 8/2003 | Ali et al. |
| 6,606,512 B2 | 8/2003 | Muz et al. |
| 6,615,064 B1 | 9/2003 | Aldrich |
| 6,615,065 B1 | 9/2003 | Barrett et al. |
| 6,618,602 B2 | 9/2003 | Levin et al. |
| 6,622,034 B1 | 9/2003 | Gorski et al. |
| 6,628,975 B1 | 9/2003 | Fein et al. |
| 6,631,281 B1 | 10/2003 | Kästle |
| 6,643,530 B2 | 11/2003 | Diab et al. |
| 6,643,531 B1 | 11/2003 | Katarow |
| 6,647,279 B2 | 11/2003 | Pologe |
| 6,647,280 B2 | 11/2003 | Bahr et al. |
| 6,650,917 B2 | 11/2003 | Diab et al. |
| 6,650,918 B2 | 11/2003 | Terry |
| 6,654,621 B2 | 11/2003 | Palatnik et al. |
| 6,654,622 B1 | 11/2003 | Eberhard et al. |
| 6,654,623 B1 | 11/2003 | Kästle |
| 6,654,624 B2 | 11/2003 | Diab et al. |
| 6,658,276 B2 | 12/2003 | Kianl et al. |
| 6,658,277 B2 | 12/2003 | Wassermann |
| 6,662,033 B2 | 12/2003 | Casciani et al. |
| 6,665,551 B1 | 12/2003 | Suzuki |
| 6,668,182 B2 | 12/2003 | Hubelbank |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,671,530 B2 | 12/2003 | Chung et al. |
| 6,671,531 B2 | 12/2003 | Al-Ali et al. |
| 6,671,532 B1 | 12/2003 | Fudge et al. |
| 6,675,031 B1 | 1/2004 | Porges et al. |
| 6,678,543 B2 | 1/2004 | Diab et al. |
| 6,681,126 B2 | 1/2004 | Solenberger |
| 6,681,128 B2 | 1/2004 | Steuer et al. |
| 6,681,454 B2 | 1/2004 | Modgil et al. |
| 6,684,090 B2 | 1/2004 | Ali et al. |
| 6,684,091 B2 | 1/2004 | Parker |
| 6,694,160 B2 | 2/2004 | Chin |
| 6,697,653 B2 | 2/2004 | Hanna |
| 6,697,655 B2 | 2/2004 | Sueppel et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,699,199 B2 | 3/2004 | Asada et al. |
| 6,701,170 B2 | 3/2004 | Stetson |
| 6,702,752 B2 | 3/2004 | Dekker |
| 6,707,257 B2 | 3/2004 | Norris |
| 6,708,049 B1 | 3/2004 | Berson et al. |
| 6,709,402 B2 | 3/2004 | Dekker |

| | | |
|---|---|---|
| 6,711,424 B1 | 3/2004 | Fine et al. |
| 6,711,425 B1 | 3/2004 | Reuss |
| 6,714,803 B1 | 3/2004 | Mortz |
| 6,714,804 B2 | 3/2004 | Al-Ali et al. |
| 6,714,805 B2 | 3/2004 | Jeon et al. |
| RE38,492 E | 4/2004 | Diab et al. |
| 6,719,686 B2 | 4/2004 | Coakley et al. |
| 6,719,705 B2 | 4/2004 | Mills |
| 6,720,734 B2 | 4/2004 | Norris |
| 6,721,584 B2 | 4/2004 | Baker, Jr. et al. |
| 6,721,585 B1 | 4/2004 | Parker |
| 6,725,074 B1 | 4/2004 | Kästle |
| 6,725,075 B2 | 4/2004 | Al-Ali |
| 6,731,963 B2 | 5/2004 | Finarov et al. |
| 6,731,967 B1 | 5/2004 | Turcott |
| 6,735,459 B2 | 5/2004 | Parker |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neil et al. |
| 6,754,515 B1 | 6/2004 | Pologe |
| 6,754,516 B2 | 6/2004 | Mannheimer |
| 6,760,607 B2 | 7/2004 | Al-Ali |
| 6,760,609 B2 | 7/2004 | Jacques |
| 6,760,610 B2 | 7/2004 | Tscupp et al. |
| 6,763,255 B2 | 7/2004 | DeLonzor et al. |
| 6,763,256 B2 | 7/2004 | Kimball et al. |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,792,300 B1 | 9/2004 | Diab et al. |
| 6,793,654 B2 | 9/2004 | Lemberg |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,801,802 B2 | 10/2004 | Sitzman et al. |
| 6,802,812 B1 | 10/2004 | Walker et al. |
| 6,805,673 B2 | 10/2004 | Dekker |
| 6,810,277 B2 | 10/2004 | Edgar, Jr. et al. |
| 6,813,511 B2 | 11/2004 | Diab et al. |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,830,711 B2 | 12/2004 | Mills et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,839,659 B2 | 1/2005 | Tarassenko et al. |
| 6,842,635 B1 | 1/2005 | Parker |
| 6,845,256 B2* | 1/2005 | Chin et al. .................. 600/323 |
| 6,850,787 B2 | 2/2005 | Weber et al. |
| 6,850,788 B2 | 2/2005 | Al-Ali |
| 6,850,789 B2 | 2/2005 | Schweitzer, Jr. et al. |
| 6,861,639 B2 | 3/2005 | Al-Ali |
| 6,863,652 B2 | 3/2005 | Huang et al. |
| 6,865,407 B2 | 3/2005 | Kimball et al. |
| 6,879,850 B2 | 4/2005 | Kimball |
| 6,882,874 B2 | 4/2005 | Huiku |
| 6,889,153 B2 | 5/2005 | Dietiker |
| 6,898,452 B2 | 5/2005 | Al-Ali et al. |
| 6,909,912 B2 | 6/2005 | Melker et al. |
| 6,912,413 B2 | 6/2005 | Rantala et al. |
| 6,916,289 B2 | 7/2005 | Schnall |
| 6,920,345 B2 | 7/2005 | Al-Ali et al. |
| 6,931,269 B2 | 8/2005 | Terry |
| 6,934,570 B2 | 8/2005 | Kiani et al. |
| 6,939,307 B1 | 9/2005 | Dunlop |
| 6,941,162 B2 | 9/2005 | Fudge et al. |
| 6,947,781 B2 | 9/2005 | Asada et al. |
| 6,950,687 B2 | 9/2005 | Al-Ali |
| 6,963,767 B2 | 11/2005 | Rantala et al. |
| 6,971,580 B2 | 12/2005 | Zhu et al. |
| 6,983,178 B2 | 1/2006 | Fine et al. |
| 6,985,763 B2 | 1/2006 | Boas et al. |
| 6,985,764 B2 | 1/2006 | Mason et al. |
| 6,990,426 B2 | 1/2006 | Yoon et al. |
| 6,992,751 B2 | 1/2006 | Okita et al. |
| 6,992,772 B2 | 1/2006 | Block et al. |
| 6,993,371 B2 | 1/2006 | Kiani et al. |
| 6,993,372 B2 | 1/2006 | Fine et al. |
| 6,996,427 B2 | 2/2006 | Ali et al. |
| 7,003,338 B2 | 2/2006 | Weber et al. |
| 7,003,339 B2 | 2/2006 | Diab et al. |
| 7,006,855 B1 | 2/2006 | Sarussi |
| 7,006,856 B2 | 2/2006 | Baker, Jr. et al. |
| 7,016,715 B2 | 3/2006 | Stetson |
| 7,020,507 B2 | 3/2006 | Scharf et al. |
| 7,024,233 B2 | 4/2006 | Ali et al. |
| 7,024,235 B2 | 4/2006 | Melker et al. |
| 7,025,728 B2 | 4/2006 | Ito et al. |
| 7,027,849 B2 | 4/2006 | Al-Ali et al. |
| 7,027,850 B2 | 4/2006 | Wasserman |
| 7,035,697 B1 | 4/2006 | Brown |
| 7,039,449 B2 | 5/2006 | Al-Ali |
| 7,043,289 B2 | 5/2006 | Fine et al. |
| 7,047,055 B2 | 5/2006 | Boaz et al. |
| 7,047,056 B2* | 5/2006 | Hannula et al. .............. 600/340 |
| 7,060,035 B2 | 6/2006 | Wasserman et al. |
| 7,062,307 B2 | 6/2006 | Norris et al. |
| 7,067,893 B2 | 6/2006 | Mills et al. |
| 7,072,701 B2 | 7/2006 | Chen et al. |
| 7,072,702 B2 | 7/2006 | Edgar, Jr. et al. |
| 7,079,880 B2 | 7/2006 | Stetson |
| 7,085,597 B2 | 8/2006 | Fein et al. |
| 7,096,052 B2 | 8/2006 | Mason et al. |
| 7,096,054 B2 | 8/2006 | Adbul-Hafiz et al. |
| 7,107,088 B2 | 9/2006 | Aceti |
| 7,113,815 B2 | 9/2006 | O'Neil et al. |
| 7,123,950 B2 | 10/2006 | Mannheimer |
| 7,127,278 B2 | 10/2006 | Melker et al. |
| 7,130,671 B2 | 10/2006 | Baker, Jr. et al. |
| 7,132,641 B2 | 11/2006 | Schulz et al. |
| 7,133,711 B2 | 11/2006 | Chernoguz et al. |
| 7,139,559 B2 | 11/2006 | Kenagy et al. |
| 7,142,901 B2 | 11/2006 | Kiani et al. |
| 7,162,288 B2 | 1/2007 | Nordstrom |
| 7,190,987 B2 | 3/2007 | Lindekugel et al. |
| 7,198,778 B2 | 4/2007 | Achilefu et al. |
| 7,209,775 B2 | 4/2007 | Bae et al. |
| 7,215,984 B2 | 5/2007 | Diab et al. |
| 7,215,991 B2 | 5/2007 | Besson et al. |
| 7,218,966 B2 | 5/2007 | Haefner |
| 7,225,006 B2 | 5/2007 | Al-Ali et al. |
| 7,225,007 B2 | 5/2007 | Al-Ali et al. |
| 7,236,811 B2 | 6/2007 | Schmitt |
| 7,236,881 B2 | 6/2007 | Liu et al. |
| 7,248,910 B2 | 7/2007 | Li et al. |
| 7,254,433 B2 | 8/2007 | Diab et al. |
| 7,254,434 B2 | 8/2007 | Schulz et al. |
| 7,263,395 B2 | 8/2007 | Chan et al. |
| 7,272,426 B2 | 9/2007 | Schmid |
| 7,280,858 B2 | 10/2007 | Al-Ali et al. |
| 7,295,866 B2 | 11/2007 | Al-Ali et al. |
| 7,305,262 B2 | 12/2007 | Brodnick et al. |
| 7,315,753 B2 | 1/2008 | Baker, Jr. et al. |
| 7,340,287 B2 | 3/2008 | Mason et al. |
| 7,650,177 B2* | 1/2010 | Hoarau et al. ................ 600/344 |
| 7,657,294 B2* | 2/2010 | Eghbal et al. ................ 600/344 |
| 7,657,296 B2* | 2/2010 | Raridan et al. ............... 600/344 |
| 7,684,843 B2* | 3/2010 | Coakley et al. .............. 600/344 |

| Patent/Publication | Date | Inventor |
|---|---|---|
| 7,693,559 B2 * | 4/2010 | Raridan et al. ............... 600/344 |
| 2001/0021803 A1 | 9/2001 | Blank et al. |
| 2001/0051767 A1 | 12/2001 | Williams et al. |
| 2002/0026109 A1 | 2/2002 | Diab et al. |
| 2002/0028990 A1 | 3/2002 | Sheperd et al. |
| 2002/0038078 A1 | 3/2002 | Ito |
| 2002/0042558 A1 | 4/2002 | Mendelson |
| 2002/0068859 A1 | 6/2002 | Knopp |
| 2002/0128544 A1 | 9/2002 | Diab et al. |
| 2002/0133067 A1 | 9/2002 | Jackson, III |
| 2002/0156354 A1 | 10/2002 | Larson |
| 2002/0173706 A1 | 11/2002 | Takatani |
| 2002/0173709 A1 | 11/2002 | Fine et al. |
| 2002/0190863 A1 | 12/2002 | Lynn |
| 2002/0198442 A1 | 12/2002 | Rantala et al. |
| 2003/0018243 A1 | 1/2003 | Gerhardt et al. |
| 2003/0036690 A1 | 2/2003 | Geddes et al. |
| 2003/0045785 A1 | 3/2003 | Diab et al. |
| 2003/0073889 A1 | 4/2003 | Keilbach et al. |
| 2003/0073890 A1 | 4/2003 | Hanna |
| 2003/0100840 A1 | 5/2003 | Sugiura et al. |
| 2003/0132495 A1 | 7/2003 | Mills et al. |
| 2003/0135099 A1 | 7/2003 | Al-Ali |
| 2003/0162414 A1 | 8/2003 | Schulz et al. |
| 2003/0171662 A1 | 9/2003 | O'Connor et al. |
| 2003/0176776 A1 | 9/2003 | Huiku |
| 2003/0181799 A1 | 9/2003 | Lindekugel et al. |
| 2003/0187337 A1 | 10/2003 | Tarassenko et al. |
| 2003/0195402 A1 | 10/2003 | Fein et al. |
| 2003/0197679 A1 | 10/2003 | Ali et al. |
| 2003/0212316 A1 | 11/2003 | Leiden et al. |
| 2003/0225323 A1 | 12/2003 | Kiani et al. |
| 2003/0225337 A1 | 12/2003 | Scharf et al. |
| 2003/0236452 A1 | 12/2003 | Melker et al. |
| 2003/0236647 A1 | 12/2003 | Yoon et al. |
| 2004/0006261 A1 | 1/2004 | Swedlow et al. |
| 2004/0010188 A1 | 1/2004 | Wasserman et al. |
| 2004/0024297 A1 | 2/2004 | Chen et al. |
| 2004/0024326 A1 | 2/2004 | Yeo et al. |
| 2004/0034293 A1 | 2/2004 | Kimball |
| 2004/0039272 A1 | 2/2004 | Abdul-Hafiz et al. |
| 2004/0039273 A1 | 2/2004 | Terry |
| 2004/0054269 A1 | 3/2004 | Rantala et al. |
| 2004/0054291 A1 | 3/2004 | Schulz et al. |
| 2004/0059209 A1 | 3/2004 | Al-Ali et al. |
| 2004/0059210 A1 | 3/2004 | Stetson |
| 2004/0064020 A1 | 4/2004 | Diab et al. |
| 2004/0068164 A1 | 4/2004 | Diab et al. |
| 2004/0087846 A1 | 5/2004 | Wasserman |
| 2004/0092805 A1 | 5/2004 | Yarita |
| 2004/0097797 A1 | 5/2004 | Porges et al. |
| 2004/0098009 A1 | 5/2004 | Boecker et al. |
| 2004/0107065 A1 | 6/2004 | Al-Ali et al. |
| 2004/0116788 A1 | 6/2004 | Chernoguz et al. |
| 2004/0116789 A1 | 6/2004 | Boaz et al. |
| 2004/0117891 A1 | 6/2004 | Hannula et al. |
| 2004/0122300 A1 | 6/2004 | Boas et al. |
| 2004/0122302 A1 | 6/2004 | Mason et al. |
| 2004/0133087 A1 | 7/2004 | Ali et al. |
| 2004/0133088 A1 | 7/2004 | Al-Ali et al. |
| 2004/0138538 A1 | 7/2004 | Stetson |
| 2004/0138540 A1 | 7/2004 | Baker, Jr. et al. |
| 2004/0143172 A1 | 7/2004 | Fudge et al. |
| 2004/0147821 A1 | 7/2004 | Al-Ali et al. |
| 2004/0147822 A1 | 7/2004 | Al-Ali et al. |
| 2004/0147823 A1 | 7/2004 | Kiani et al. |
| 2004/0147824 A1 | 7/2004 | Diab et al. |
| 2004/0152965 A1 | 8/2004 | Diab et al. |
| 2004/0158134 A1 | 8/2004 | Diab et al. |
| 2004/0158135 A1 | 8/2004 | Baker, Jr. et al. |
| 2004/0162472 A1 | 8/2004 | Berson et al. |
| 2004/0171920 A1 | 9/2004 | Mannheimer et al. |
| 2004/0171948 A1 | 9/2004 | Terry |
| 2004/0176671 A1 | 9/2004 | Fine et al. |
| 2004/0181133 A1 | 9/2004 | Al-Ali et al. |
| 2004/0181134 A1 | 9/2004 | Baker, Jr. et al. |
| 2004/0186358 A1 | 9/2004 | Chernow et al. |
| 2004/0199063 A1 | 10/2004 | O'Neil et al. |
| 2004/0204636 A1 | 10/2004 | Diab et al. |
| 2004/0204637 A1 | 10/2004 | Diab et al. |
| 2004/0204638 A1 | 10/2004 | Diab et al. |
| 2004/0204639 A1 | 10/2004 | Casciani et al. |
| 2004/0204865 A1 | 10/2004 | Lee et al. |
| 2004/0210146 A1 | 10/2004 | Diab et al. |
| 2004/0215069 A1 | 10/2004 | Mannheimer |
| 2004/0230107 A1 | 11/2004 | Asada et al. |
| 2004/0230108 A1 | 11/2004 | Melker et al. |
| 2004/0236196 A1 | 11/2004 | Diab et al. |
| 2004/0242980 A1 | 12/2004 | Kiani et al. |
| 2004/0249252 A1 | 12/2004 | Fine et al. |
| 2004/0257557 A1 | 12/2004 | Block et al. |
| 2004/0260161 A1 | 12/2004 | Melker et al. |
| 2004/0267103 A1 | 12/2004 | Li et al. |
| 2004/0267104 A1 | 12/2004 | Hannula et al. |
| 2004/0267140 A1 | 12/2004 | Ito et al. |
| 2005/0004479 A1 | 1/2005 | Townsend et al. |
| 2005/0010092 A1 | 1/2005 | Weber et al. |
| 2005/0020887 A1 | 1/2005 | Goldberg |
| 2005/0020894 A1 | 1/2005 | Norris et al. |
| 2005/0033128 A1 | 2/2005 | Ali et al. |
| 2005/0033129 A1 | 2/2005 | Edgar, Jr. et al. |
| 2005/0043599 A1 | 2/2005 | O'Mara |
| 2005/0043600 A1 | 2/2005 | Diab et al. |
| 2005/0049470 A1 | 3/2005 | Terry |
| 2005/0049471 A1 | 3/2005 | Aceti |
| 2005/0075550 A1 | 4/2005 | Lindekugel |
| 2005/0113656 A1 | 5/2005 | Chance |
| 2005/0119708 A1 | 6/2005 | Haefner |
| 2005/0177034 A1 | 8/2005 | Beaumont |
| 2005/0197548 A1 | 9/2005 | Dietiker |
| 2005/0228248 A1 | 10/2005 | Dietiker |
| 2005/0277819 A1 | 12/2005 | Kiani et al. |
| 2005/0280531 A1 | 12/2005 | Fadem et al. |
| 2005/0283059 A1 | 12/2005 | Iyer et al. |
| 2006/0058594 A1 | 3/2006 | Ishizuka et al. |
| 2006/0084852 A1 | 4/2006 | Mason et al. |
| 2006/0089547 A1 | 4/2006 | Sarussi |
| 2006/0106294 A1 | 5/2006 | Maser et al. |
| 2006/0195028 A1 | 8/2006 | Hannula et al. |
| 2006/0224058 A1 | 10/2006 | Mannheimer |
| 2006/0247501 A1 | 11/2006 | Ali |
| 2006/0258921 A1 | 11/2006 | Addison et al. |
| 2007/0032709 A1 | 2/2007 | Coakley et al. |
| 2007/0032710 A1 | 2/2007 | Raridan et al. |
| 2007/0032715 A1 | 2/2007 | Eghbal et al. |
| 2007/0073126 A1 | 3/2007 | Raridan, Jr. |
| 2007/0078311 A1 | 4/2007 | Al-Ali et al. |
| 2007/0078317 A1 | 4/2007 | Matlock |
| 2007/0112260 A1 | 5/2007 | Diab et al. |
| 2007/0208235 A1 | 9/2007 | Besson et al. |
| 2007/0208269 A1 | 9/2007 | Mumford et al. |
| 2007/0244378 A1 | 10/2007 | Al Ali et al. |
| 2007/0282178 A1 | 12/2007 | Scholler et al. |
| 2007/0282183 A1 | 12/2007 | Scholler et al. |
| 2007/0293896 A1 | 12/2007 | Haefner |
| 2008/0081492 A1 | 4/2008 | Sawatari et al. |
| 2008/0081508 A1 | 4/2008 | Sawatari et al. |
| 2008/0146890 A1 | 6/2008 | Leboeuf et al. |
| 2008/0197301 A1 | 8/2008 | Diab |
| 2008/0255435 A1 | 10/2008 | Al-Ali et al. |
| 2008/0294209 A1 | 11/2008 | Thompson et al. |

FOREIGN PATENT DOCUMENTS

| | | |
|---|---|---|
| DE | 3703458 | 8/1988 |
| DE | 19632361 | 2/1997 |

| | | |
|---|---|---|
| DE | 19640807 | 9/1997 |
| EP | 0127947 | 12/1984 |
| EP | 0531631 | 3/1993 |
| EP | 0724860 | 8/1996 |
| EP | 1491135 | 12/2004 |
| FR | 2685865 | 7/1993 |
| JP | 2111343 | 4/1990 |
| JP | 3116259 | 5/1991 |
| JP | 3116260 | 5/1991 |
| JP | 3245042 | 10/1991 |
| JP | 5049625 | 3/1993 |
| JP | 6014906 | 1/1994 |
| JP | 6269430 | 9/1994 |
| JP | 7001273 | 1/1995 |
| JP | 7136150 | 5/1995 |
| JP | 7236625 | 9/1995 |
| JP | 10216115 | 8/1998 |
| JP | 10337282 | 12/1998 |
| JP | 2000237170 | 9/2000 |
| JP | 2004159810 | 6/2004 |
| JP | 2004248820 | 9/2004 |
| JP | 2004261364 | 9/2004 |
| JP | 2004329406 | 11/2004 |
| JP | 2004337605 | 12/2004 |
| JP | 2004344367 | 12/2004 |
| JP | 2004351107 | 12/2004 |
| WO | WO8909566 | 10/1989 |
| WO | WO9001293 | 2/1990 |
| WO | WO9111137 | 8/1991 |
| WO | WO9309711 | 5/1993 |
| WO | WO9502358 | 1/1995 |
| WO | WO9736536 | 10/1997 |
| WO | WO9857577 | 12/1998 |
| WO | WO9947039 | 9/1999 |
| WO | WO0059374 | 10/2000 |
| WO | WO0117421 | 3/2001 |
| WO | 2005010568 | 2/2005 |
| WO | WO2005010567 | 2/2005 |
| WO | WO2005010568 | 2/2005 |
| WO | 2007097754 | 2/2006 |
| WO | 2007133947 | 11/2007 |

OTHER PUBLICATIONS

Izumi, Akio, et al.; "Accuracy and Utility of a New Reflectance Pulse Oximeter for Fetal Monitoring During Labor," Journal of Clinical Monitoring, vol. 13, pp. 103-108 (1997).

"Smaller Product, Tighter Tolerances Pose Dispensing Challenges for Medical Device Manufacturer," Adhesives Age, pp. 40-41 (Oct. 1997).

Crilly, Paul B., et al.; "An Integrated Pulse Oximeter System for Telemedicine Applications," IEEE Instrumentation and Measurement Technology Conference, Ottawa, Canada; May 19-21, 1997; pp. 102-104.

DeKock, Marc; "Pulse Oximetry Probe Adhesive Disks: a Potential for Infant Aspiration," Anesthesiology, vol. 89, pp. 1603-1604 (1998).

Yang, Boo-Ho, et al.; "A Twenty-Four Hour Tele-Nursing System Using a Ring Sensor," Proceedings of the 1998 IEEE International Conference on Robotics & Automation, Leaven, Belgium, May 1998; pp. 387-392.

Such Hans Olaf; "Optoelectronic Non-invasive Vascular Diagnostics Using multiple Wavelength and Imaging Approach," Dissertation, (1998).

Ferrell, T.L., et al.; "Medical Telesensors," SPIE, vol. 3253, pp. 193-198 (1998).

Ikeda, Kenji, et al.; "Improvement of Photo-Electric Plethysmograph Applying Newly Developed Opto-Electronic Devices," IEEE Tencon, pp. 1109-1112 (1999).

Yang, Boo-Ho, et al.; "Development to the ring sensor for healthcare automation," Robotics and Autonomous Systems, vol. 30, pp. 273-281 (2000).

Rhee, Sokwoo, et al.; "Artifact-Resistant, Power-Efficient Design of Finger-Ring Plethysmographic Sensor—Part I: Design and Analysis," Proceedings of the 22nd Annual EMBS International Conference, Chicago, Illinois; Jul. 23-38, 2000; pp. 2792-2795.

Rhee, Sokwoo, et al.; "Artifact-Resistant, Power-Efficient Design of Finger-Ring Plethysmographic Sensor—Part II: Prototyping and Benchmarking," Proceedings of the 22nd Annual EMBS International Conference, Chicago, Illinois; Jul. 23-28, 2000; p. 2796.

Schulz, Christian Eric; "Design of a Pulse Oximetry Sensor Housing Assembly," California State University Master's Thesis, UMI Dissertation Services, UMI No. 1401306, (May 2000) 63 pages.

Aoyagi, T., et al.; "Pulse Oximeters: background, present and future," Neonatal Care, vol. 13, No. 7, pp. 21-27 (2000) (Article in Japanese—contains English summary of article).

Yokota, Nakaura, Takahashi, et al.; "Pilot Model of a Reflectance-Type Pulse Oximeter for Pre-hospital Evaluation," Journal of the Japanese Society of Emergency Medicine, Kanto Region, vol. 21, pp. 26-27 (2000) (Article in Japanese—contains English summary.

Gisiger, P.A., et al.; "OxiCarbo®, a single sensor for the non-invasive measurement of arterial oxygen saturation and CO2 partial pressure at the ear lobe," Sensor and Actuators, vol. B-76, pp. 527-530 (2001).

Cysewska-Sobusaik, Anna; "Metrological Problems With noninvasive Transillumination of Living Tissues," Proceedings of SPIE, vol. 4515, pp. 15-24 (2001).

Rhee, Sokwoo, et al.; "Artifact-Resistant, Power-Efficient Design of Finger-Ring Plethysmographic Sensor," IEEE Transactions on Biomedical Engineering, vol. 48, No. 7, pp. 795-805 (Jul. 2001).

Lopez-Sliva, Sonnia Maria Lopez, et al.; "NIR transmittance pulse oximetry system with laser diodes," Clinical Diagnostic Systems, Proceedings of SPIE, vol. 4255, pp. 80-87 (2001).

Maletras, Francois-Xavier, et al.; "Construction and calibration of a new design of Fiber Optic Respiratory Plethysmograph (FORP)," Optomechanical Design and Engineering, Proceedings of SPIE, vol. 4444, pp. 285-293 (2001).

Earthrowl-Gould, T., et al.; "Chest and abdominal surface motion measurement for continuous monitoring of respiratory function," Proc. Instn Mech Engrs, V215, Part H; pp. 515-520 (2001).

Relente, A.R., et al.; "Characterization and Adaptive Filtering of Motion Artifacts in Pulse Oximetry using Accelerometers," Proceedings of the Second joint EMBS/BMES Conference, Houston, Texas, Oct. 23-26, 2002; pp. 1769-1770.

Tobata, H., et al.; "Study of Ambient Light Affecting Pulse Oximeter Probes," Ikigaku (Medical Technology), vol. 71, No. 10, pp. 475-476 (2002) (Article in Japanese—contains English summary of article).

Irie, A., et al.; "Respiration Monitors—Pulse Oximeters," Neonatal Care, vol. 15, No. 12, pp. 78-83 (2002) (Article in Japanese—contains English summary of article).

Shaltis, Phillip, et al.; "Implementation and Validation of a Power-Efficient, High-Speed Modulation Design for Wireless Oxygen Saturation Measurement Systems," IEEE, pp. 193-194 (2002).

Warren, Steve, et al.; "Wearable Sensors and Component-Based Design for Home Health Care," Proceedings of the Second Joint EMBS/BMES Conference, Houston, Texas; Oct. 23-26, 2002; pp. 1871-1872.

Cyrill, D., et al.; "Adaptive Comb Filter for Quasi-Periodic Physiologic Signals," Proceedings of the 25th Annual International Conference of the IEEE EMBS, Cancun, Mexico, Sep. 17-21, 2003; pp. 2439-2442.

Aoyagi, Takuo; "Pulse oximetry: its invention, theory, and future," Journal of Anesthesia, vol. 17, pp. 259-266 (2003).

Itoh, K., et al.; "Pulse Oximeter," Toyaku Zasshi (Toyaku Journal), vol. 25, No. 8, pp. 50-54 (2003) (Article in Japanese—contains English summary of article).

Matsui, A., et al.; "Pulse Oximeter," Neonatal Care, vol. 16, No. 3, pp. 38-45 (2003) (Article in Japanese—contains English summary of article).

Nakagawa, M., et al.; "Oxygen Saturation Monitor," Neonatal Monitoring, vol. 26, No. 5, pp. 536-539 (2003) (Article in Japanese—contains English summary of article).

Johnston William S., et al.; "Effects of Motion Artifacts on helmet-Mounted Pulse Oximeter Sensors," 2 pgs. (2004).

Matsuzawa, Y., et al.; "Pulse Oximeter," Home Care Medicine, pp. 42-45 (Jul. 2004); (Article in Japanese—contains English summary of article).

Urquhart, C., et al.; "Ear probe pulse oximeters and neonates," Anaesthesia, vol. 60, p. 294 (2005).

Bentley, David J. et al.; "Measure Pressure with Thin Film"; Paper Film & Foil Converter; May 1, 2003.

Rhee, Sokwoo, et al.; "The Ring Sensor: A New Ambulatory Wearable Sensor for Twenty-Four Hour Patient Monitoring," Proceedings of the 20th Annual International Conference of the IEEE Engineering in Medicine and Biology Society, vol. 20, No. 4, pp. 1906-1919; published Oct. 29-Nov. 1, 1998.

Odagiri, Y.; "Pulse Wave Measuring Device," Micromechatronics, vol. 42, No. 3, pp. 6-11; published Sep. 1998; (Article in Japanese—contains English summary of article).

http://www.fcw.com.my/fujifilm.html; last viewed on Jun. 25, 2008.

US 4,928,691, 05/1990, Nicolson et al. (withdrawn)

* cited by examiner

SYSTEM AND METHOD FOR COATING AND SHIELDING ELECTRONIC SENSOR COMPONENTS

BACKGROUND

The present disclosure relates generally to medical devices and, more particularly, to sensors used for sensing physiological parameters of a patient.

This section is intended to introduce the reader to aspects of the art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices and techniques have been developed for monitoring physiological characteristics. Such devices and techniques provide doctors and other healthcare personnel with the information they need to provide the best possible healthcare for their patients. As a result, these monitoring devices and techniques have become an indispensable part of modern medicine.

One such monitoring technique is commonly referred to as pulse oximetry. Pulse oximetry may be used to measure various blood flow characteristics, such as the blood-oxygen saturation of hemoglobin in arterial blood and/or the rate of blood pulsations corresponding to each heartbeat of a patient.

The devices based upon pulse oximetry techniques are commonly referred to as pulse oximeters. Pulse oximeters typically utilize a non-invasive sensor that is placed on or against a patient's tissue that is well perfused with blood, such as a patient's finger, toe, forehead or earlobe. The pulse oximeter sensor emits light and photoelectrically senses the absorption and/or scattering of the light after passage through the perfused tissue. A photo-plethysmographic waveform, which corresponds to the cyclic attenuation of optical energy through the patient's tissue, may be generated from the detected light. Additionally, one or more physiological characteristics may be calculated based upon the amount of light absorbed or scattered. More specifically, the light passed through the tissue may be selected to be of one or more wavelengths that may be absorbed or scattered by the blood in an amount correlative to the amount of the blood constituent present in the blood. The amount of light absorbed and/or scattered may then be used to estimate the amount of blood constituent in the tissue using various algorithms.

For example, a reflectance-type sensor placed on a patient's forehead may emit light into the skin and detect the light that is "reflected" back after being transmitted through the forehead tissue. A transmission-type sensor may be placed on a finger; wherein the light waves are emitted through and detected on the opposite side of a finger. In either case, the amount of light detected may provide information that corresponds to valuable physiological patient data. The data collected by the sensor may be used to calculate one or more of the above physiological characteristics based upon the absorption or scattering of the light. For instance, the emitted light is typically selected to be of one or more wavelengths that are absorbed or scattered in an amount related to the presence of oxygenated versus de-oxygenated hemoglobin in the blood. The amount of light absorbed and/or scattered may be used to estimate the amount of the oxygen in the tissue using various algorithms.

The sensors generally include an emitter that emits the light and a detector that detects the light. The emitter and detector may be located on a flexible circuit that allows the sensor to conform to the appropriate site on the patient's skin, thereby making the procedure more comfortable for a patient. During use, the emitter and detector may be held against the patient's skin to facilitate the light being directed into and received from the skin of the patient. For example, the sensor may be applied to a patient's forehead. To aid in the sensor's proper placement and the proper application of pressure by the sensor to the forehead site, some forehead sensors are maintained at the forehead site by either the assistance of an adhesive layer, a headband or a hat. Any number of methods may be used to press the sensor against the patient's skin to facilitate the light being directed into and received from the skin of the patient.

A properly fitted sensor will allow the emitted light to travel through the tissue of the site and be detected without additional light being introduced, thereby preventing measurement distortion. However, in practice, the design of the sensor may not provide a tight fit between the sensor and the surface of the patient's skin. Further, to reduce measurement error, protective layers may be applied to the sensors to prevent external light from being detected by the sensor. In certain places on the flexible circuit, protective layers may delaminate, leading to shunting, where light is transmitted directly between the emitter and detector, leading to inaccurate measurements. In addition, layers added to the sensor may be uncomfortable to the patient, especially if they are delaminating.

Moreover, to increase accuracy, a photodetector of the sensor may be encompassed by a layer of wire mesh to shield the photodetector from external electromagnetic fields. The wire mesh layer may contribute to the delamination of the light blocking layer, exacerbating the shunting and measurement issues. Further, proper application of the light-blocking layer and the wire mesh layer can be time consuming. There is a need, therefore, for an improved arrangement for blocking external light and external static fields that will improve accuracy and comfort of the sensor.

BRIEF DESCRIPTION OF THE DRAWINGS

Advantages of the disclosure may become apparent upon reading the following detailed description and upon reference to the drawings in which.

DETAILED DESCRIPTION

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

As described herein, various embodiments of sensors are provided featuring various coatings to prevent shunting and interference from external light as well as external electromagnetic forces. Further the embodiments of sensors discussed are designed to fit a range of patient application areas and are designed to provide a simplified method for manufacturing. In general, embodiments of the sensors include optical components or devices (e.g., emitters and detectors) that are coated with a polymeric material that blocks the passage of unwanted light from external sources as well as directly between the emitter and detector. In further embodiments, some or all of the optical components may be coated with an additional layer of conductive polymeric material that prevents or reduces external static forces.

Figure 1:
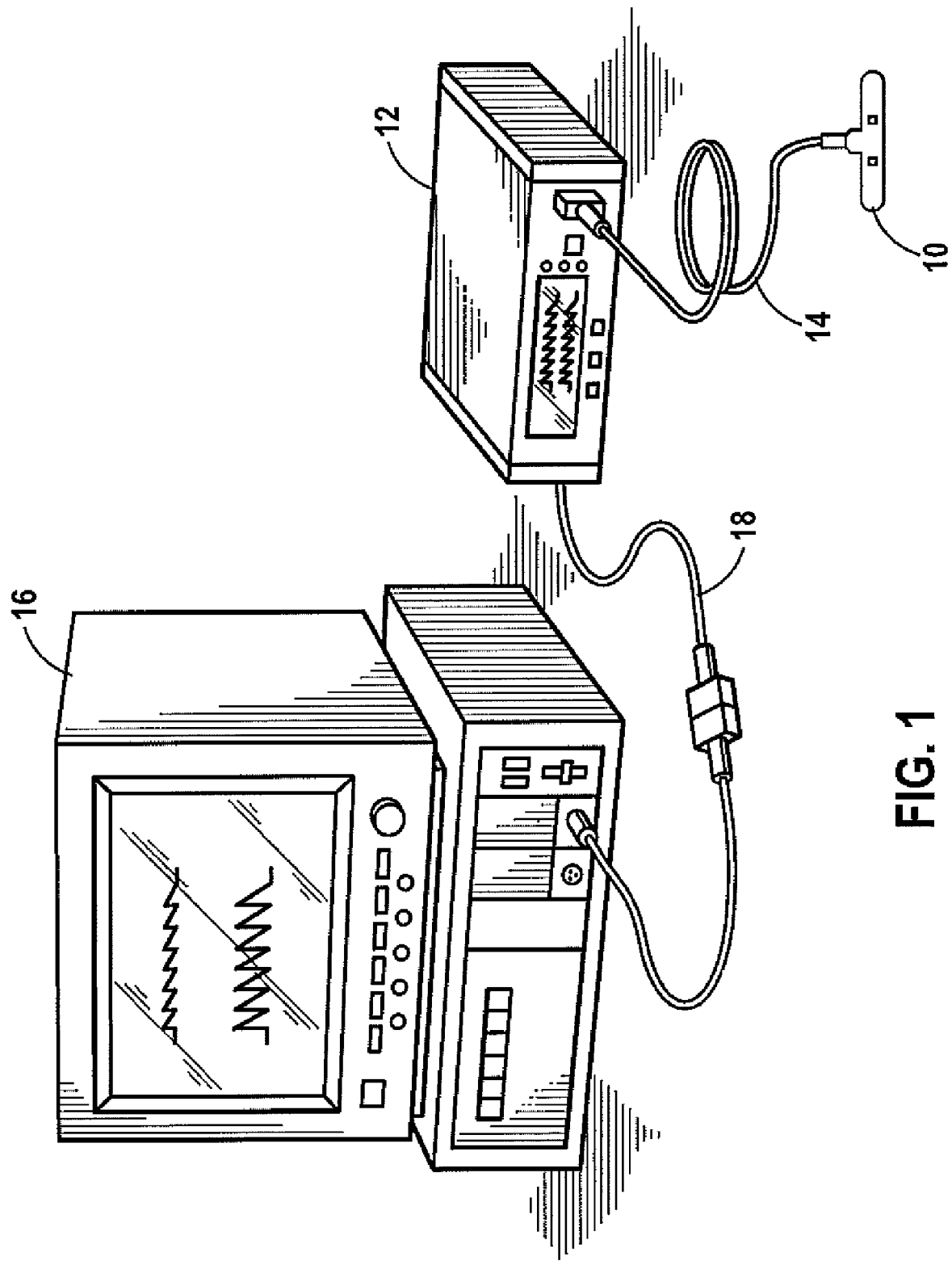
FIG. 1 illustrates a patient monitoring system coupled to a multi-parameter patient monitor and a sensor assembly including an optical sensor, in accordance with an embodiment.

Prior to discussing such sensors in detail, it should be appreciated that such sensors are typically designed for use with a patient monitoring system. For example, referring now to FIG. 1, sensor 10 may be used in conjunction with patient monitor 12. Sensor 10, as depicted in FIG. 1, may be designed to be placed on a patient's forehead, either inside a hat or a headband or with an adhesive. In the depicted embodiment, cable 14 connects sensor 10 to patient monitor 12. Sensor 10 and/or cable 14 may include or incorporate one or more integrated circuit or electrical devices, such as a memory processor chip, that may facilitate or enhance communication between sensor 10 and patent monitor 12. Similarly, cable 14 may be an adaptor cable, with or without an integrated circuit or electrical device, for facilitating communication between sensor 10 and various types of monitors, including different versions of patient monitor 12 or other physiological monitors. In other embodiments, sensor 10 and patient monitor 12 may communicate via wireless means, such as using radio frequency, infrared or optical signals. In such embodiments, a transmission device may be connected to sensor 10 to facilitate wireless transmission between sensor 10 and patient monitor 12. Cable 14 (or a corresponding wireless connection) may typically be used to transmit control or timing signals from patient monitor 12 to sensor 10 and/or to transmit acquired data from sensor 10 to patient monitor 12. In other embodiments, the cable 14 may be an optical fiber that enables optical signals to be transmitted between patient monitor 12 and sensor 10.

In one embodiment, patient monitor 12 may be a suitable pulse oximeter, such as those available from Nellcor Puritan Bennett L.L.C. In other embodiments, patient monitor 12 may be a monitor suitable for measuring tissue water fractions, or other body fluid related metrics, using spectrophotometric or other techniques. Furthermore, patient monitor 12 may be a multipurpose monitor suitable for performing pulse oximetry and measurement of tissue water fraction, or other combinations of physiological and/or biochemical monitoring processes, using data acquired via the sensor 10 and/or other sensors. Moreover, to upgrade conventional monitoring functions provided by the system, patient monitor 12 may be coupled to a multi-parameter patient monitor 16 via cable 18 connected to a sensor input port and/or a cable connected to a digital communication port.

Figure 2:
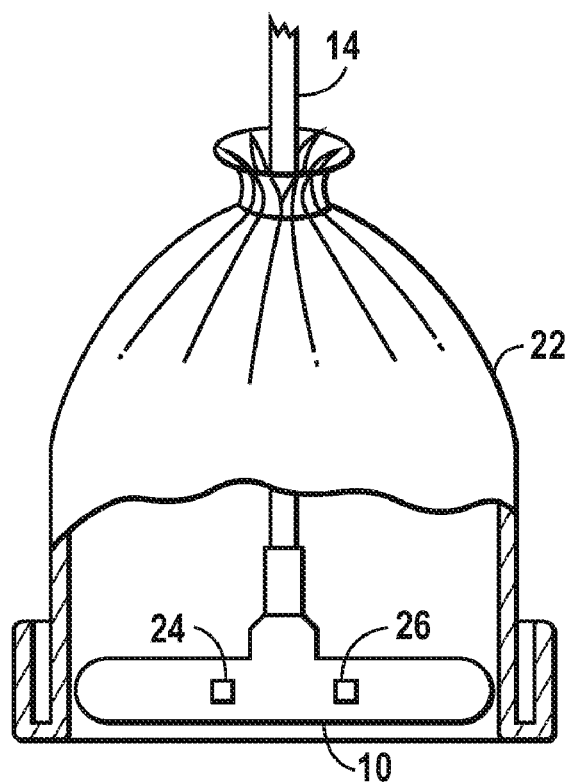
FIG. 2 is a drawing of a hat, with an embodiment of the presently disclosed sensor assembly mounted in the hat.

Turning now to FIG. 2, an embodiment of sensor 10 is shown inside a hat 22. The sensor may be placed inside hat 22, such as a stocking cap, so that sensor 10 may be placed on the patient's forehead area. Sensor 10 includes optical devices, such as emitter 24 and detector 26, which may be of any suitable type. For example, emitter 24 may be one or more light emitting diodes adapted to transmit one or more wavelengths of light, such as a red to infrared range, and detector 26 may be a photodetector, such as a silicon photodiode package, selected to receive light in the range emitted from emitter 24. In the embodiment, sensor 10 is coupled to cable 14 that may be used to transmit electrical and/or optical signals to and from emitter 24 and detector 26. Cable 14 may be permanently coupled to sensor 10, or it may be removably coupled to sensor 10. The removable coupling of cable 14 may be utilized in situations where sensor 10 is disposable, e.g., where a sensor is disposed of after being used on a patient.

Sensor 10, as discussed herein, may be configured for reflective type sensing. Furthermore, sensor 10 may include various structural and functional features designed to facilitate its use. An example of one such sensor and its use and construction may be found in U.S. application Ser. No. 11/199,524 titled "Medical sensor and Technique for Using the Same" and filed on Aug. 8, 2005, which is herein incorporated by reference in its entirety for all purposes. However other suitable sensor packages may also be used in conjunction with the presently disclosed techniques and devices. In the illustrated embodiment, sensor 10 includes a flexible circuit, on which emitter 24 and detector 26 may be mounted. The flexible circuit may be used to transmit signals to emitter 24 and from detector 26 via cable 14. A detailed discussion of the components of sensor 10 will be addressed below.

With regard to the location of the sensor 10 on the patient's forehead, the sensor may be situated on the lower forehead region, above the eyebrow, with the sensor optical devices located above and predominantly lateral to or centered over the iris. In the depicted embodiment, the sensor 10 may be attached to the inside band of hat 22. The precise location of the reflectance sensor in the hat allows appropriate placement of the sensor in the optimal forehead location by a user not skilled in sensor placement. It has been found that the placement of a reflectance forehead sensor is a factor in the accurate determination of a blood flow characteristic, due to the vasculature of the forehead. In addition, it has been shown that having a certain amount of pressure on the forehead sensor can reduce the incidence of venous pulsations effects on the oximeter reading. The placement of the sensor 10 in the band of the hat 22 may minimize these issues, as the placement of a hat is a fairly repeatable and predictable process. A hat-based sensor 10, as embodied by the present disclosure, may be used on patients in clinical settings, or by athletes, soldiers, firemen, or in any environment where information related to a physiological parameter, such as heart rate or oxygen saturation information is desired.

Figure 3:
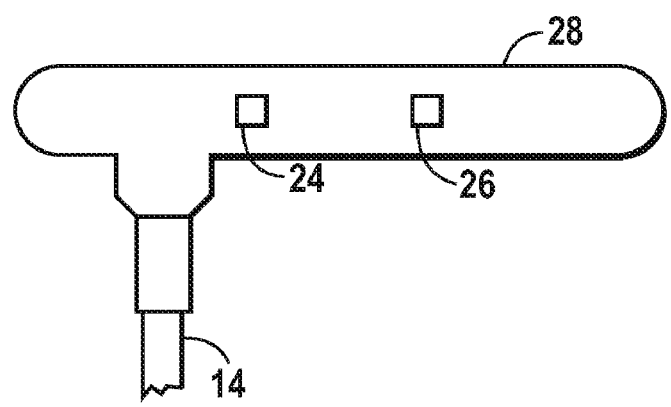
FIG. 3 is a top view of a sensor assembly having a bandage style configuration, in accordance with an embodiment.

In some situations, a user may desire to place the sensor on a perfused area of the body by means of a flexible bandage. An embodiment that depicts such a bandage style sensor 28 is shown in FIG. 3. As depicted, the bandage style sensor 28 may include optical components such as emitter 24 and detector 26. In one embodiment, the bandage style sensor 28 may use an adhesive layer to attach the sensor 28 to the patient's skin. The adhesive layer may include an acrylic or synthetic rubber adhesive. Alternatively, in another embodiment, the bandage style sensor 28 may be applied without adhesive, instead being made from a foam PVC or foam polyurethane material and attached to the skin by medical tape. In one embodiment, the face or skin contacting side of the bandage sensor 28 is black so as to minimize the incidence of reflected light that does not go through the tissue. Bandage style sensor 28 may also include a flexible circuit which may be used to transmit signals to emitter 24 and from detector 26 via cable 14. The bandage style sensor 28 may be adhered to a patient's forehead, finger, toe, or suitably perfused area of the body.

Figure 4:
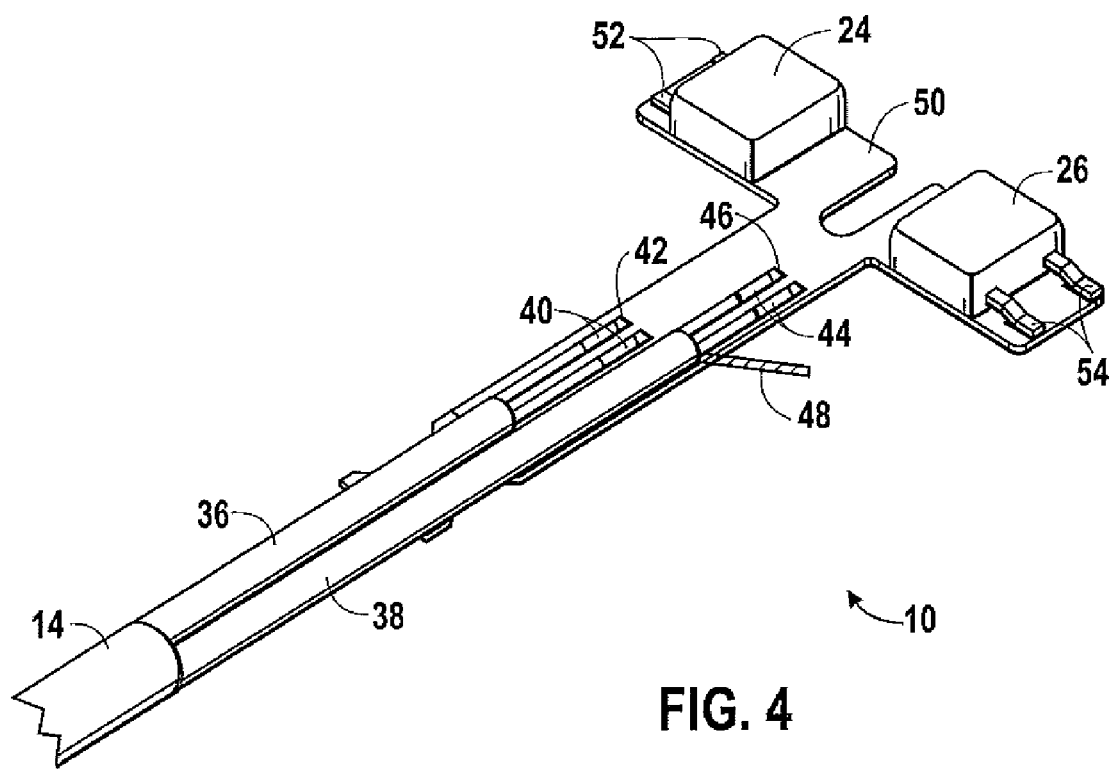
FIG. 4 is a perspective view of the optical sensor assembly, including an emitter and a detector, in accordance an embodiment.

FIG. 4 depicts a detailed illustration of sensor 10 prior to protection and/or shielding via a coating or other technique, as will be described below. In an embodiment, sensor 10 includes emitter 24 and detector 26 which transmit signals to a monitor via emitter line 36 and detector line 38, respectively within the cable 14. As depicted, emitter line 36 and detector line 38 may each be encompassed by a rubber material to insulate the wires from interference from external sources or each other. Further, cable 14 may include a rubber insulator that encompasses emitter line 36 and detector line 38. In the embodiment, emitter line 36 may include several wires 40 such as a positive and/or negative signal connection lead, which may be attached to emitter connection 42 via solder or other appropriate means. Similarly, detector line 38 may include wires 44 that may rout signals from detector 26 via detector connection 46. In one embodiment, detector line 38 also includes ground wire 48 which may be used to connect the monitor to a conductive Faraday shield or other conductive coating on the sensor. As previously discussed, signals may be routed between emitter 24, detector 26 and their respective lines via a flexible circuit or substrate, indicated in the embodiment by numeral 50. In an embodiment, signals may be routed from emitter connection 42 and detector connection 46 via flexible circuit 50 to emitter pins 52 and detector pins 54. Emitter pins 52 may be used to transmit signals and/or power from flex circuit 50 to emitter 24. Similarly, detector pins 54 may transmit signals and/or power to or from detector 26.

In the illustrated embodiment, flexible circuit 50 includes a plurality of electrical traces that may facilitate the transmission of power and other signals to or from the optical components. Accordingly, in an embodiment in which sensor 10 includes emitter 24, flexible circuit 50 may drive emission of one or more wavelengths emitted by emitter 24. In an embodiment in which sensor 10 includes detector 26, the flexible circuit 50 may transmit signals indicative of the light received by detector 26. Further, flexible circuit 50 may provide structural support to emitter 24 and detector 26, while allowing sensor 10 to conform to the shape of the desired region of the patient's skin. In one embodiment, the flexible circuit 50 may allow sensor 10, whether bandage, hat-style or other configuration, to be applied to and conform to a patient's skin region. In one embodiment, a hat-style sensor 10 may conform to the shape of a patient's forehead due in part to the flexibility and/or conformability of flex circuit 50, which provides solid contact between the optical components and the skin. In one hat-based embodiment, the sensor 10 may use an emitter 24, capable of emitting two discrete wavelengths and a detector 26, placed more than 2 mm away from emitter 24. In one such embodiment, the emitter 24 and detector 26 are spaced about 10-15 mm apart.

In some embodiments, the sensor 10 may only include one optical device. For example, a sensor assembly may only include an emitter which may be connected to an oximeter monitor. A separate sensor, containing a detector may also be connected to the oximeter monitor. The monitor may be used to synchronize the separate emitter and detector devices in order to acquire accurate measurements. In this embodiment, the separate emitter assembly and detector assembly may include coatings and/or layers, as discussed herein, that are tailored to the shielding and/or protection requirements for each optical device.

Figure 5:
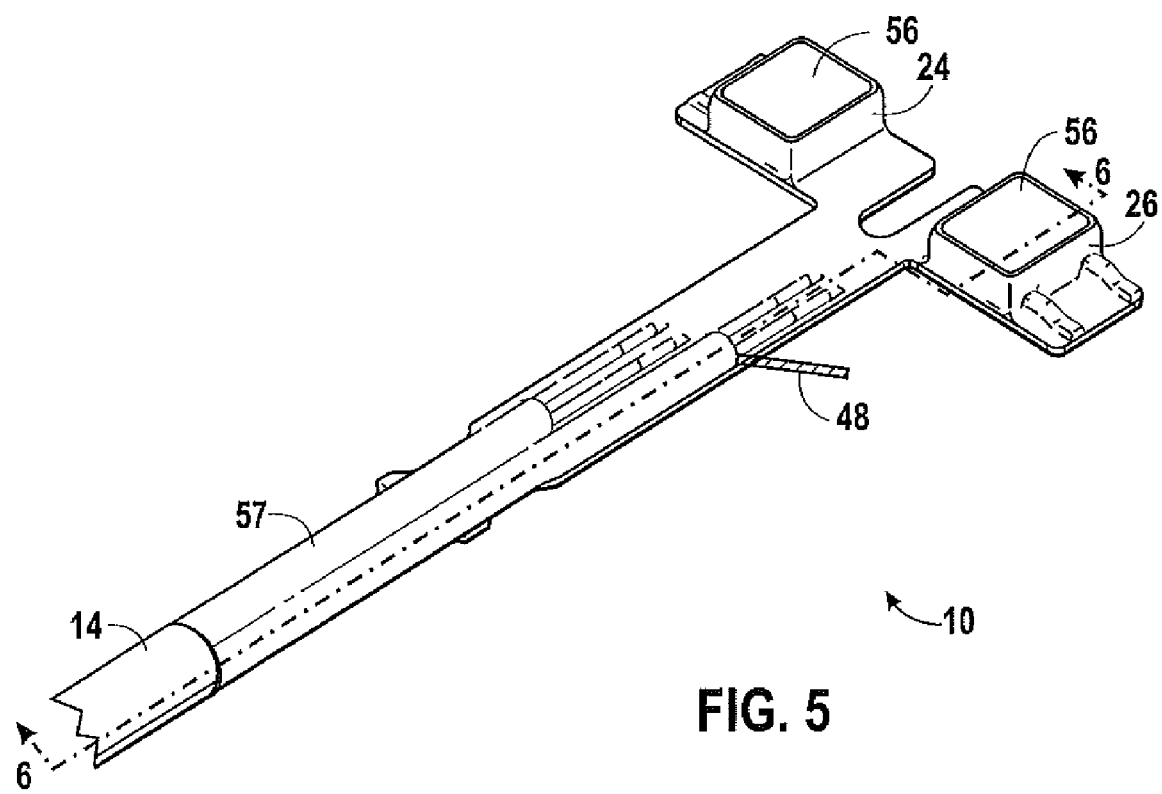
FIG. 5 is a perspective view of the optical sensor assembly shown in FIG. 4 with a coating applied, in accordance with an embodiment.

FIG. 5 illustrates an embodiment of sensor 10 wherein the sensor depicted in FIG. 4 has one coating or layer applied to protect and shield one or more of the optical components. The illustration also includes sectional line 6 depicting the staggered vertical plane used to construct the sectional views depicted in FIGS. 6-8. In one embodiment, emitter 24 and detector 26 feature active faces 56 of the optical devices which are generally the surfaces of the devices that receive or emit light and are located on the skin contacting side of the device.

As illustrated, a first coating 57 may cover some or all of the flexible circuit, a portion of emitter 24 and detector 26 and the exposed portion of wires 40 and 44. In one such embodiment a mask or other means, such as tape, for covering emitter 24 or detector 26 may be used to cover the active faces 56 of the optical components while first coating 57 is applied. The first coating 57 may be applied by dipping the flex circuit 50 and the attached optical components in a suitable unset coating material, such that, when removed, a first coating 57 of the desired thickness coats some or all of the flex circuit 50, the emitter 24 and the detector 26. First coating 57 may include a polymeric material such as silicone, neoprene, isoprene or other suitable nonconductive material. In one embodiment, first coating 57 may be composed of a medical grade silicone that is approximately 0.015 inch thick. After the coating material has dried, the mask over the active faces 56 may be removed, thereby removing the coating from the active faces and allowing emitter 24 and detector 26 to receive or transmit light waves. For example, in the depicted embodiment, the sensor 10 is depicted after a first coating 57 has been applied and the masks have been removed. As discussed herein, in other embodiments in which additional layers or coatings are applied, the masks may not be removed until the last layer of coating is applied and set.

In certain embodiments, the coating material 57 may provide an opaque or light blocking layer to prevent shunting between emitter 24 and detector 26 and to prevent external light from affecting the measurements. Further, the coating 57 may provide a seal around the cables, wires and flexible circuit, thereby reducing the likelihood of substances from contacting the sensor components. In other embodiments, the coatings or layers may be applied by spraying, molding or using other appropriate means to apply the desired material around sensor 10 and its components.

Figure 6:
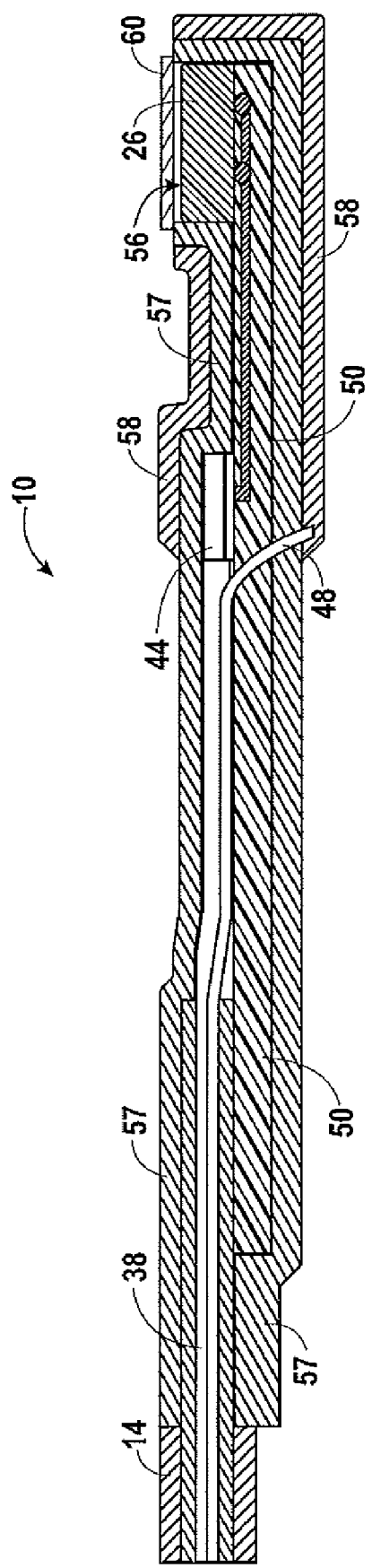
FIG. 6 is a sectional view of an embodiment of the optical sensor assembly, including a coating and a layer, in accordance with an embodiment.

Certain embodiments may include only a few layers to shield and/or protect the emitter 24 and detector 26 from external sources that may interfere with the oximeter measurement. For example, as depicted in the embodiment of FIG. 6, first coating 57 of sensor 10 may contain an opaque and non-conductive material, thereby shielding the optical devices from external light and preventing shunting between emitter 24 and detector 26. In one embodiment, the first coating may encompass the entire flex circuit 50 and a portion of the optical devices including the sides of detector 26. In the depicted embodiment, the active face 56 of detector 26 is not coated by the first coating 57. It should be noted that although the sectional illustration shows only detector 26 and its coatings, emitter 24 may feature the same or similar coatings as depicted with respect to detector 26. For example, in one embodiment, first coating 57 may be disposed over the entire flex circuit 50 of sensor 10. However, in another embodiment, first coating 57 is only disposed over the portion of sensor 10 requiring protection, e.g., wire leads 40, emitter 24 and detector 26.

In one embodiment, a Faraday shield 58 may be applied over all or part of the first coating 57. The Faraday shield 58 may be composed of a conductive material to shield the optical devices from external static fields. For example, in one embodiment the Faraday shield may be composed of a copper mesh or other suitable conductive material in order to prevent degradation of the measurement signal by external static fields. In one such embodiment, Faraday shield 58 covers the optical devices and wire leads 40. Thus, the Faraday shield 58 may be used to shield wire leads and the optical devices from external static electric fields, thereby protecting the signal until it is routed to the insulated cable assemblies. In one such embodiment, the Faraday shield may be disposed on the entire length of the flex circuit 50, protecting the entire sensor 10 from external electromagnetic fields though in other embodiments, the Faraday shield 58 may be disposed on less than the entire length of the flex circuit 50. As depicted, ground wire 48 may be connected to Faraday shield 58 in certain embodiments, thereby providing a connection to ground for Faraday shield 58 via cable to a monitor.

In one embodiment, window 60 may be placed on the outer-most coating of sensor 10, thereby permitting the optical devices to emit and/or detect light without obstruction by the protected layers and/or coatings. Window 60 may be composed of any suitable transparent material, such as polyurethane that may protect the optical components while allowing light transmission to the components. The use of the term "transparent" herein to describe the window 60 generally denotes that the window 60 may freely pass the wavelengths of light emitted by the emitter 24 or detected by detector 26 with little or no degradation or attenuation. The window 60, however, may or may not allow other wavelengths to be transmitted or may reduce or attenuate such other wavelengths. In one embodiment, window 60 is placed on an opening in Faraday shield 58, which exposes active face 56 to a patient's skin.

During use of the sensor 10, windows 60 may contact a patient's skin to facilitate the transmission of light between the emitter 24, detector 26 and the patient's skin and tissue. For example, in one embodiment, the detector 26 may be disposed internal to the coatings and window 60 such that it has a clear line of sight to and through the window 60. In one embodiment, emitter 24 may be subjected to the same coatings, protections and manufacturing processes and, therefore, the descriptions of detector 26 may also pertain to the fabrication of emitter 24.

Figure 7:
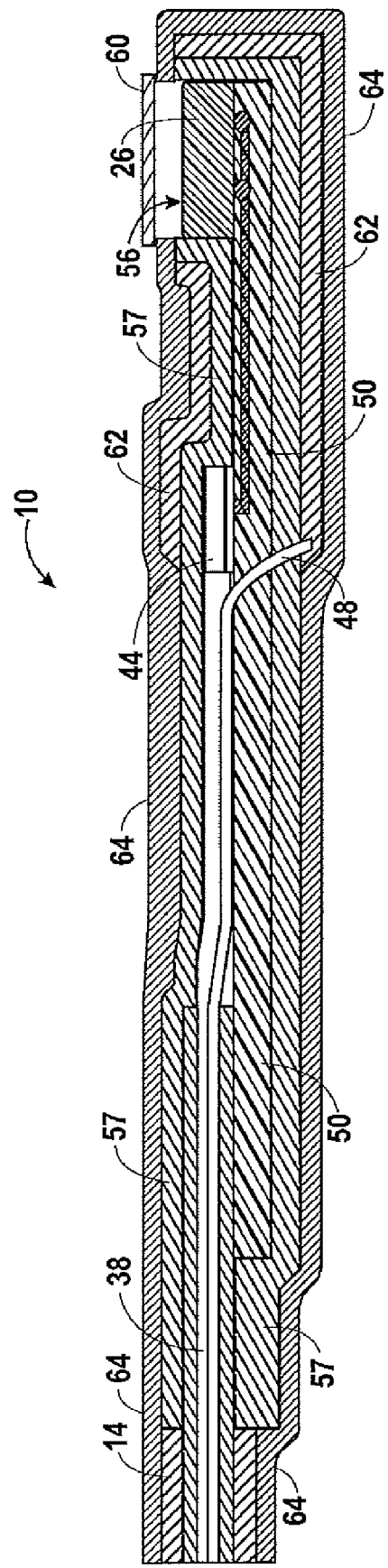
FIG. 7 is a sectional view of the optical sensor assembly, including a layer and coatings, in accordance with a further embodiment.

The number of and configuration of coatings and/or layers of sensor 10 may be varied in number or combination depending on several factors, such as cost, durability manufacturing limitations and size/weight constraints. A particular application may require more insulation from the Faraday shield 58 and increased durability for repeated use of the sensor than is provided by the embodiment of FIG. 6. In one embodiment, additional coatings may be applied to the sensor 10 to improve sensor performance and/or sensor comfort and durability. For example, as depicted in FIG. 7, second coating 62 may be applied after first coating 57 has been applied and has cured. In one such embodiment, the second coating 62 may be applied while the optical components are masked. The second coating 62 may be applied by dipping the flexible circuit 50 and desired optical components in a suitable unset overmold material, as previously discussed. In other embodiments, the second coating 62 may be applied by spraying on the overmold material or by using injection molding techniques.

In an embodiment, second coating 62 may be approximately the same thickness as the first coating 57, about 0.015 inch thick in one embodiment. Second coating 62 may include a polymeric composition, such as rubber or silicone, which includes a conductive material, thereby providing a Faraday shield for sensor 10. For example, in one embodiment, the conductive material included in the polymeric composition may be metallic micro-diameter beads and/or a conductive polymer, such as conductive nylon or conductive polyester urethane. In one embodiment, second coating 62 may be provided around the exposed wire leads, such as wire leads 40, as well as the optical devices, such as detector 26. In another embodiment, second coating 62 may be disposed over the entire first coating 57, thereby providing a Faraday shield for the entire sensor 10. In another embodiment, the bulk of sensor 10 may be reduced by the application of second coating 62 to only a portion of the sensor 10. Second coating 62 may be configured to allow detection of light waves from active face 56 of detector 26, via window 60. As previously described, during the application of coatings and/or layers of sensor 10, active face 56 of detector 26 may be masked over to allow the optical devices to remain uncovered when the mask is removed after application of the desired coating layers.

In an embodiment, third coating 64 may be applied to the outer portion of second coating 62 and a portion of first coating 57. In one embodiment, third coating 64 is applied by masking the optical components and dipping the flexible circuit 50 and desired optical components in a suitable unset overmold material, such as a polymeric composition. In other embodiments, the third coating 64 may be applied by spraying or injection molding the overmold material. In an embodiment, third coating 64 may be substantially thicker than first coating 57, such as 0.03125 inch thick, to provide structural support to sensor 10. In one embodiment, third coating 64 contains a non-conductive material, thereby preventing any electrical exchange between the sensor 10 and the environment. In one embodiment, third coating 64 may be disposed over the entire surface of sensor 10 and a portion of monitor cable 14, thereby providing strain relief between sensor 10 and cable 14. In another embodiment, third coating 64 may only be disposed on the outer portion of second coating 62, thereby protecting an operator or patient from electrostatic charges. In one embodiment, window 60 is placed on third coating 64, enabling the optical device to transmit or receive wavelengths of light through the window.

The thickness of first coating 57, second coating 62 and third coating 64 may depend on the desired properties of the coating or layering materials, the cost of materials, manufacturing limitations, size, weight, and/or other constraints. First coating 57, second coating 62 and third coating 64 may each be formed from one or more suitable polymeric compositions, such as a silicone, neoprene, isoprene or other suitable materials. In the case of second coating 62, the material may include an additive that has the desired conductive properties. The amount of additive needed to achieve the desired conductive properties may depend on several factors, such as environment and other application-specific facts. Examples of silicones that may be utilized for the sensor coatings include Dow Corning Silastic® Silicone Rubber or Dow Corning Dispersion Material. For example, the Silastic® rubber material may be applied by dipping the sensor in the material or injecting the material into a mold around the sensor. The Dispersion Material may be applied by spraying or dipping the sensor in the material. Moreover, the chosen material, whether Silastic®, Dispersion material or some other polymeric composition may be pigmented or may contain an opaque additive, such as carbon granules, to achieve the opacity desired for the designated coating or layer. For example, a Silastic® rubber, when used as first coating 57 may include an added pigment to achieve the opacity needed to block the wavelengths of light. The chosen pigmentation might make the material opaque to all light wavelengths or may be designed to only block those wavelengths that may affect the oximeter measurement.

Figure 8:
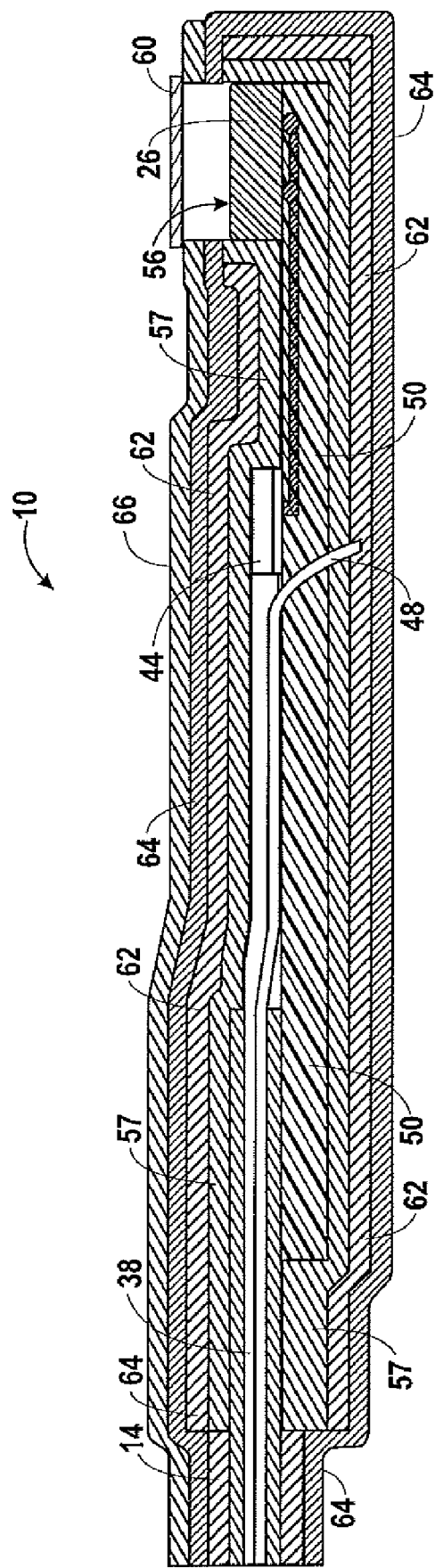
FIG. 8 is a sectional view of the optical sensor assembly, including two coatings and layers, in accordance with an additional embodiment.

In some applications, it may be desirable to provide multiple overmold layers, as discussed above, in conjunction with a flexible and comfortable sensor surface to contact the patient's skin. FIG. 8 illustrates an embodiment of sensor 10 that provides such a skin contacting layer 66 to enhance the sensor's overall comfort. As depicted, sensor 10 features the first coating 57, containing a non-conductive, opaque material that may be disposed around sensor 10 and exposes the active faces 56 of emitter 24 and detector 26. Second coating 62 may include a conductive material that acts as a Faraday shield for sensor 10. In the embodiment, second layer 62 may be disposed on top of first coating 57 and also provides an opening for active faces 56 of the optical devices. As depicted, the non-conductive third coating 64 is disposed on second layer 62 and also exposes active faces 56 of the optical devices. In the embodiment, ground wire 48 may provide a ground connection to conductive second coating 62. Further, wire lead 40 may be connected to detector connection point 44 to transmit signals to emitter 24. As depicted, a skin contacting layer 66 may be located on the skin contacting side of sensor 10. In one embodiment skin contacting layer 66 may be made of a material that conforms as the sensor is pressed against a patient's skin, such as Poron®, a foam PVC or foam polyurethane material. Moreover, window 60 may be applied to skin contacting layer 66, thereby protecting and allowing light to enter or leave the active faces 56 of the optical devices.

While the disclosure may be susceptible to various modifications and alternative forms, specific embodiments have been shown by way of example in the drawings and have been described in detail herein. However, it should be understood that the disclosure is not intended to be limited to the particular forms provided. Rather, the disclosure is to cover all modifications, equivalents, and alternatives falling within the spirit and scope of the disclosure as defined by the following appended claims. Indeed, the present disclosed methods may not only be applied to transmission type sensors for use in pulse oximetry, but also to other sensor designs. Likewise, the present disclosure is not limited to use on foreheads but may also be applied to placement on other body parts.

What is claimed is:

1. A sensor assembly, comprising:
   a flexible circuit comprising an optical device having an active face; and
   a coating coated on a portion of the flexible circuit and capable of inhibiting light from reaching the optical device other than at the active face, wherein the coating comprises a generally opaque, nonconductive material capable of inhibiting the passage of one or more wavelengths of light.

2. The sensor assembly of claim 1, wherein the coating comprises a medical grade silicone.

3. The sensor assembly of claim 1, comprising a conductive layer disposed on at least part of the coating.

4. The sensor assembly of claim 3, wherein the conductive layer comprises a generally metallic mesh material.

5. The sensor assembly of claim 3, wherein the conductive layer comprises metallic micro-diameter beads and/or a conductive polymer.

6. The sensor assembly of claim 3, wherein the conductive layer comprises a conductive nylon and/or a conductive polyester urethane additive.

7. The sensor assembly of claim 1, wherein the coating comprises a neoprene, and/or an isoprene.

8. The sensor assembly of claim 1, wherein the coating has a thickness between about 0.005 inch and about 0.020 inch.

9. A flexible circuit assembly, comprising:
   a first optical device capable of emitting light;
   a second optical device capable of receiving the light emitted from the first optical device after passing through tissue; and
   a coating disposed over the first and second optical devices by dipping, spraying, or molding, wherein the coating comprises a generally opaque, nonconductive material capable of inhibiting the direct transmission of light from the first optical device to the second optical device.

10. The flexible circuit assembly of claim 9, wherein the coating comprises a medical grade silicone.

11. The flexible circuit assembly of claim 9, comprising a conductive layer disposed on at least part of the coating.

12. The flexible circuit assembly of claim 11, wherein the conductive layer comprises a generally metallic mesh material.

13. The flexible circuit assembly of claim 11, wherein the conductive layer comprises metallic micro-diameter beads or a conductive polymer.

14. The flexible circuit assembly of claim 11, wherein the conductive layer comprises a conductive nylon and/or a conductive polyester urethane.

15. The flexible circuit assembly of claim 9, wherein the coating comprises a neoprene, and/or an isoprene.

16. The flexible circuit assembly of claim 9, wherein the coating has a thickness between about 0.005 inch and about 0.020 inch.

17. A sensor assembly, comprising:
    a flexible circuit assembly, comprising:
      a first optical device capable of emitting light;
      a second optical device capable of receiving the light from the first optical device, after passing through tissue;
    a first coating disposed over the first and second optical devices, wherein the first coating comprises a generally opaque, nonconductive material capable of inhibiting the direct transmission of light from the first optical device to the second optical device; and
    a second coating disposed over the first coating, wherein the second coating comprises a conductive material.

18. The sensor assembly of claim 17, comprising a third coating disposed over the second coating, wherein the third coating comprises a generally nonconductive material.

19. The sensor assembly of claim 18, comprising a skin contacting layer disposed on one side of the third coating of the flexible circuit.

20. The sensor assembly of claim 19, comprising at least one window layer disposed on the skin contacting layer.

21. The sensor assembly of claim 17, wherein the first coating comprises a medical grade silicone having a thickness between about 0.005 inch and about 0.020 inch.

* * * * *